US008673300B2

(12) United States Patent
Eisenbarth et al.

(10) Patent No.: US 8,673,300 B2
(45) Date of Patent: Mar. 18, 2014

(54) THERAPEUTIC COMPOSITIONS AND METHODS FOR THE PREVENTION OF AUTOIMMUNE DISEASES

(75) Inventors: George Eisenbarth, Golden, CO (US); Li Zhang, Aurora, CO (US); John Kappler, Denver, CO (US); Brian Stadinski, N. Easton, MA (US)

(73) Assignees: The Regents of the University of Colorado, a body corporate, Denver, CO (US); National Jewish Health, Denver, CO (US)

( * ) Notice: Subject to any disclaimer, the term of this patent is extended or adjusted under 35 U.S.C. 154(b) by 0 days.

(21) Appl. No.: 13/376,122

(22) PCT Filed: Jun. 3, 2010

(86) PCT No.: PCT/US2010/037166
§ 371 (c)(1),
(2), (4) Date: Mar. 19, 2012

(87) PCT Pub. No.: WO2010/141658
PCT Pub. Date: Dec. 9, 2010

(65) Prior Publication Data
US 2012/0171212 A1    Jul. 5, 2012

Related U.S. Application Data

(60) Provisional application No. 61/184,106, filed on Jun. 4, 2009.

(51) Int. Cl.
*A61K 39/395* (2006.01)
*A61K 39/00* (2006.01)
*C07K 16/00* (2006.01)
*C12P 21/08* (2006.01)

(52) U.S. Cl.
USPC ............. 424/130.1; 424/135.1; 424/141.1; 530/387.1; 530/387.3; 530/388.1

(58) Field of Classification Search
None
See application file for complete search history.

(56) References Cited

U.S. PATENT DOCUMENTS

| 5,594,100 | A | 1/1997 | Wegmann |
| 8,314,210 | B2 | 11/2012 | Wucherpfennig et al. |
| 2002/0150914 | A1* | 10/2002 | Andersen et al. ............ 435/6 |
| 2004/0137514 | A1 | 7/2004 | Steenbakkers |
| 2007/0196369 | A1 | 8/2007 | Hoogenboom et al. |

FOREIGN PATENT DOCUMENTS

| WO | WO 03/070752 | 8/2003 |
| WO | WO 2004/007528 | 1/2004 |

OTHER PUBLICATIONS

Sosinowski, T., and Eisenbarth, G.S., Immunol Res. 2013;55:270-276.*
Aharoni, R., et al. Nature. 1991:351:147-150.*
Puri, J., et al. J. Immunol. 1997;158:2471-2476.*
Aoki et al., "NOD mice and autoimmunity," Autoimmun. Rev., 2005, vol. 4, pp. 373-379.
Boulard et al., "An interval tightly linked to but distinct from the h2 complex controls both overt diabetes (iddl6) and chronic experimental autoimmune thyroiditis (ceatl) in nonobese diabetic mice," Diabetes, 2002, vol. 51, pp. 2141-2147.
Chung et al., "Competitive Inhibition In Vivo and Skewing of the T Cell Repertoire of Antigen-Specific CTL Priming by an Anti-Peptide-MHC Monoclonal Antibody," J. Immunol., 2001, vol. 167, pp. 699-707.
Corper et al., "A structural framework for deciphering the link between I-Ag7 and autoimmune diabetes," Science, 2000, vol. 288, pp. 505-511.
Crawford et al., "Mimotopes for Alloreactive and Conventional T Cells in a Peptide-MHC Display Library," PLoS. Biol., 2004, vol. 2, p. E90.
Faideau et al., "Expression of preproinsulin-2 gene shapes the immune response to preproinsulin in normal mice," J. Immunol., 2004, vol. 172, pp. 25-33.
Fife et al., "Insulin-induced remission in new-onset NOD mice is maintained by the PD-1-PD-L1 pathway," J. Experimental Med., 2006, vol. 203, pp. 2737-2747.
Fujisawa et al., "MHC-linked susceptibility to type 1 diabetes in the NOD mouse: further localization of Idd16 by subcongenic analysis," Ann. NY Acad. Sci., 2006, vol. 1079, pp. 118-121.
Hattori et al., "The NOD mouse: recessive diabetogenic gene within the major histocompatibility complex," Science, 1986, vol. 231, pp. 733-735.
Homann et al., "An immunologic homunculus for type 1 diabetes," J. Clin. Invest., 2006, vol. 116, pp. 1212-1215.
Hovhannisyan et al., "The role of HLA-DQ8 beta57 polymorphism in the anti-gluten T-cell response in coeliac disease," Nature, 2008, vol. 456, pp. 534-538.
Kanagawa et al., "The role of I-A7 chain in peptide binding and antigen recognition by T cells," Int Immunol., 1998, vol. 9, pp. 1523-1526.
Kobayashi et al., "Conserved T cell receptor alpha-chain induces insulin autoantibodies," Proc. Natl. Acad. Sci. USA., 2008, vol. 105, pp. 10090-10094.
Levisetti et al., "The insulin-specific T cells of nonobese diabetic mice recognize a weak MHC-binding segment in more than one form," J. Immunol., 2007, vol. 178, pp. 6051-6057.
Levisetti et al., "Weak proinsulin peptide-major histocompatibility complexes are targeted in autoimmune diabetes in mice," Diabetes, 2008, vol. 57, pp. 1852-1860.
Mareeva et al., "Antibody Specific for the Peptide-Major Histocompatibility Complex," J. Biol. Chem., 2004, vol. 279(43), pp. 44243-44249.
Moriyama et al., "Evidence for a primary islet autoantigen (preproinsulin 1) for insulitis and diabetes in the nonobese diabetic mouse," Proc. Natl Acad. Sci. USA, 2003, vol. 100, pp. 10376-10381.

(Continued)

*Primary Examiner* — Gerald R Ewoldt
(74) *Attorney, Agent, or Firm* — Sheridan Ross P.C.

(57) ABSTRACT

Antibodies specific for an MHC class II-autoantigen complex.

4 Claims, 22 Drawing Sheets

(56) References Cited

OTHER PUBLICATIONS

Nakayama et al., "Prime role for an insulin epitope in the development of type 1 diabetes in NOD mice," Nature, 2005, vol. 435, pp. 220-223.

Nakayama et al., "Priming and effector dependence on insulin B:9-23 peptide in NOD islet autoimmnnity," J. Clin. Invest., 2007, vol. 117, pp. 1835-1843.

Pietropaolo et al., "Primer: Immunity and Autoimmunity," Diabetes, 2008, vol. 57, pp. 2872-2882.

Suri et al., "The Murine Diabetogenic Class II Histocompatibility Molecule I-A (g7): Structural and Functional Properties and Specificity of Peptide Selection," Adv. Immunol., 2005, vol. 88, pp. 235-265.

Todd et al., "A molecular basis for MHC class II associated autoimmunity," Science, 1988, vol. 240, pp. 1003-1009.

Wallis et al., "Type 1 Diabetes in the BB rat: A polygenic disease," Diabetes, 2009, vol. 58(4), pp. 1007-1017.

Wicker et al., "Type 1 diabetes genes and pathways shared by humans and NOD mice," J. Autoimmun., 2005, vol. 25 (Suppl), pp. 29-33.

Zhang et al., "Immunization with an insulin peptide-MHC complex to prevent type 1 diabetes of NOD mice," Diabetes Meta Res Rev, 2011, vol. 27, pp. 784-789.

Zhong et al., "Production, specificity, and functionality of monoclonal antibodies to specific peptide-major histocompatibility complex class II complexes formed by processing of exogenous protein," Proc. Natl. Acad. Sci. USA, 1997, vol. 94, pp. 13856-13861.

\* cited by examiner

Specific Anti-IA$^{g7}$-B peptide complex antibodies were developed after immunization I-A$^{g7}$-B:12-23 immunized serum
- I-Ag7B:12-23 competition
- I-Ag7HEL11-23 competition Anti-I-Ag7 B:12-23(cps)

Concentration of protein used in competition(ug/ml)

HEL11-23 amino acid sequence in the complex:   MKRHGLDNYRGYG

Figure 6

HEL11-23 amino acid sequence in the complex: MKRHGLDNYRGYG

A. F2.24-1 monoclonal antibodies inhibit BDC12-4.1 cells stimulated by B:9-23 peptide presented by APCs.

B. F2.24-1 monoclonal antibodies inhibit BDC12-4.1 cells stimulated by plate bound I-Ag7-B:12-22RE-Reg3.

THERAPEUTIC COMPOSITIONS AND METHODS FOR THE PREVENTION OF AUTOIMMUNE DISEASES

CROSS REFERENCE TO RELATED APPLICATION

This application is a national stage application under 35 U.S.C. 371 of PCT Application No. PCT/US2010/037166 having an international filing date of Jun. 3, 2010 which designated the United States, which PCT application claimed the benefit of U.S. Provisional Application No. 61/184,106, filed Jun. 4, 2009. The entire disclosure of each of these priority documents are hereby incorporated by reference.

GOVERNMENT INTEREST

This invention was made with government support under grant numbers RO1 DK055969 and U19 AI050864 awarded by the National Institutes of Health. The government has certain rights in the invention.

REFERENCE TO SEQUENCE LISTING

This application contains a Sequence Listing submitted as an electronic text file entitled "2848-110-PCT_ST25" having a size in bytes of 3 kb, and created Oct. 14, 2013. The information contained in this electronic file is hereby incorporated by reference in its entirety pursuant to 37 CFR §1.52(e)(5).

FIELD OF THE INVENTION

The present invention is directed to therapeutic compositions and methods for the prevention or treatment of autoimmune diseases, such as type 1 diabetes.

BACKGROUND

Autoimmune disorders are diseases caused by the body producing an inappropriate immune response against its own tissues, in which the immune system creates T lymphocytes and autoantibodies that attack one's own cells, tissues, and/or organs. Researchers have identified 80-100 different autoimmune diseases and suspect at least 40 additional diseases of having an autoimmune basis.

Autoimmune disorders are classified into two types, organ-specific (directed mainly at one organ) and non-organ-specific (widely spread throughout the body). Examples of organ-specific autoimmune disorders are insulin-dependent type 1 diabetes which affects the pancreas, Hashimoto's thyroiditis and Graves' disease which affects the thyroid gland, pernicious anemia which affects the stomach, Addison's disease which affects the adrenal glands, chronic active hepatitis which affects the liver and myasthenia gravis which affects the muscle. Examples of non-organ-specific autoimmune disorders are rheumatoid arthritis, multiple sclerosis and lupus.

Autoimmune diseases are often chronic, debilitating, and life-threatening. The National Institutes of Health (NIH) estimates up to 23.5 million Americans suffer from autoimmune disease and that the prevalence is rising. It has been estimated that autoimmune diseases are among the ten leading causes of death among women in all age groups up to 65 years. Most autoimmune diseases cannot yet be treated directly, but are treated to alleviate the symptoms associated with the condition. Some of the current treatments include administration of corticosteroid drugs, non-steroidal anti-inflammatory drugs (NSAIDs) or more powerful immunosuppressant drugs such as cyclophosphamide, methotrexate and azathioprine that suppress the immune response and stop the progression of the disease. Radiation of the lymph nodes and plasmapheresis (a procedure that removes the diseased cells and harmful molecules from the blood circulation) are other ways of treating an autoimmune disease. However, these treatments often have devastating long-term side effects Thus, there exists a need in the art for safer and more effective methods for treatment and prevention of autoimmune diseases. The instant application addresses this need by describing a novel method for treatment of autoimmune diseases.

SUMMARY OF THE INVENTION

In one embodiment, the present invention includes an isolated antibody having an inhibitory or preventive activity on an autoimmune disease in an animal, wherein the antibody specifically binds to a complex comprising a class II MHC molecule and an autoantigenic peptide implicated in the autoimmune disease.

In a further embodiment, the present invention includes a method for preventing or treating an autoimmune disease comprising administering to a subject in need thereof an effective amount of a therapeutic composition comprising an antibody that specifically binds to a complex comprising a class II MHC molecule and an autoantigenic peptide implicated in the autoimmune disease.

In some embodiments, the antibody may specifically prevent or disrupt the assembly of a trimolecular complex comprising a class II MHC molecule, an autoantigen and a T cell receptor. In some embodiments, the peptide may comprise an autoantigenic peptide modified to bind in a specific register so that it is reactive with a T cell receptor specific for the autoantigenic peptide. In some embodiments, the autoimmune disease may be type 1 diabetes, pre-diabetes of type 1A, and Latent Autoimmune Diabetes in Adults (LADA). In some embodiments, the autoimmune disease may be type 1 diabetes. In some embodiments, the autoantigen may be insulin. In some embodiments, the class II MHC molecule may be I-A$^{g7}$ or a human class II MHC molecule. In some embodiments, the TCR may contain a TRAV5D-4, TRAV5-1 or TRAV10α chain. In some embodiments, the autoantigenic peptide may be peptide B:9-23 comprising SEQ ID NO:1 (SHLVEALYLVCGERG), B:12-23 comprising SEQ ID NO:2 (VEALYLVCGERG), B:12-22 comprising SEQ ID NO:3 (VEALYLVCGER), B:12-22 Reg.3 comprising SEQ ID NO:8 (VERLYLVAGEE), (RE)Reg.1 comprising SEQ ID NO:4 (LREALYLVAE), (RE)Reg.2 comprising SEQ ID NO:5 (VRALYLVAGE), (RE)Reg.3 comprising SEQ ID NO:6 (ERLYLVAGEE), (RE)Reg.4 comprising SEQ ID NO:7 (ARYLVAGERE), B:13-22 comprising SEQ ID NO:9 (EALYLVCGER), or a homolog thereof.

In some embodiments, the antibody may be humanized. In some embodiments, the antibody may be Fab, Fab', F(ab')2, or scFv fragment. In some embodiments, the antibody may be monoclonal. In some embodiments, the antibody may be administered to the animal by passive infusion. In some embodiments, the antibody may be administered to the animal in an amount of 100 µg/kg to about 10,000 µg/kg.

In a further embodiment, the present invention includes a therapeutic composition comprising a peptide attached to a class II MHC molecule for immunizing an animal in order to produce an antibody having an inhibitory or preventive activity on an autoimmune disease in the animal, wherein the peptide is an autoantigenic peptide implicated in the autoimmune disease, and the antibody specifically binds to a complex comprising the class II MHC molecule and the peptide.

In another embodiment, the present invention includes a method for preventing or treating an autoimmune disease comprising immunizing a subject with an effective amount of a therapeutic composition comprising a peptide, wherein the peptide is an autoantigenic peptide implicated in the autoimmune disease, and the immunization leads to production of an antibody that specifically binds to a complex comprising a class II MHC molecule and the peptide.

In some embodiments, the antibody may specifically prevent or disrupt the assembly of a trimolecular complex comprising a class II MHC molecule, an autoantigen and a T cell receptor. In some embodiments, the peptide may comprise an autoantigenic peptide modified to bind in a specific register so that it is reactive with a T cell receptor specific for the autoantigenic peptide. In some embodiments, the autoimmune disease may be type 1 diabetes, pre-diabetes of type 1A, and Latent Autoimmune Diabetes in Adults (LADA). In some embodiments, the autoimmune disease may be type 1 diabetes. In some embodiments, the autoantigen may be insulin. In some embodiments, the class II MHC molecule may be I-A$^{g7}$ or a human class II MHC molecule. In some embodiments, the TCR may contain a TRAV5D-4, TRAV5-1 or TRAV10 a chain. In some embodiments, the autoantigenic peptide may be peptide B:9-23 comprising SEQ ID NO:1 (SHLVEALYLVCGERG), B:12-23 comprising SEQ ID NO:2 (VEALYLVCGERG), B:12-22 comprising SEQ ID NO:3 (VEALYLVCGER), B:12-22 Reg.3 comprising SEQ ID NO:8 (VERLYLVAGEE), (RE)Reg.1 comprising SEQ ID NO:4 (LREALYLVAE), (RE)Reg.2 comprising SEQ ID NO:5 (VRALYLVAGE), (RE)Reg.3 comprising SEQ ID NO:6 (ERLYLVAGEE), (RE)Reg.4 comprising SEQ ID NO:7 (ARYLVAGERE), B:13-22 comprising SEQ ID NO:9 (EALYLVCGER), or a homolog thereof. In some embodiments, the class II MHC molecule is I-A$^{g7}$.

In some embodiments, the therapeutic composition may be a vaccine. In some embodiments, the therapeutic composition may further comprise an adjuvant. In some embodiments, the route of administration of the composition may be parenteral, intravenous, subcutaneous, oral, nasal or transcutaneous.

In some embodiments, the present invention may include a kit comprising the therapeutic composition.

In a further embodiment, the present invention includes a production method of an antibody having a therapeutic effect in an autoimmune disease, comprising an immunization step of immunizing a non-human animal with an autoantigenic peptide implicated in the autoimmune disease attached to a class II MHC molecule; a hybridoma production step of fusing an antibody producing cell taken out from the immunized non-human animal with an immortalized cell so as to obtain a hybridoma; a hybridoma selection step of selecting a hybridoma producing an antibody having a binding property to the said peptide; and an antibody separation step for separating an antibody expressed by the selected hybridoma.

BRIEF DESCRIPTION OF THE DRAWINGS

FIG. 6 shows that IA$^{g7}$-B12-23 complex absorbed the antibodies completely but the IA$^{g7}$-HEL11-23 complex did not which suggests that antibodies specific against the IA$^{g7}$-B:12-23 complex recognized by T cells exist in the serum.

FIGS. 16A and 16B show data related to stimulation of T cells by B:9-23 presented by APCs and by plate bound I-A$^{g7}$-B:12-22RE-Reg3, respectively.

FIGS. 17A and 17B show dose response data related to stimulation of T cells by B:9-23 presented by APCs and by plate bound I-A$^{g7}$-B:12-22RE-Reg3, respectively.

DETAILED DESCRIPTION OF THE INVENTION

Figure 1A:
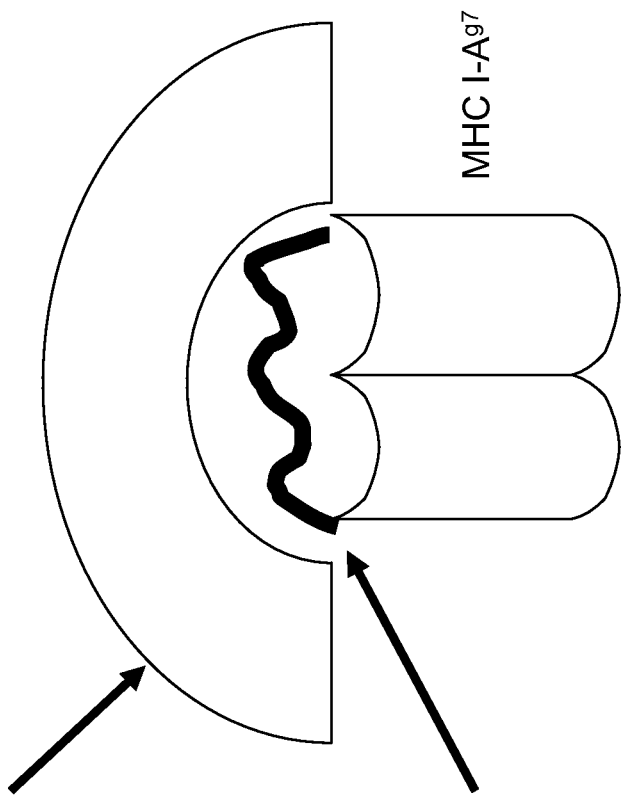
FIG. 1A shows a schematic diagram of the trimolecular complex involving MHC class II molecule (IA$^{g7}$ in mouse), Insulin B:9-23 peptide and T cell Receptor comprising TRAV5D-4*04 Vα chain.

The present invention describes a novel antigen-specific strategy for the prevention or treatment of an autoimmune disease. Recognition of an autoantigenic peptide is dependent upon presentation of the autoantigenic peptide by a specific MHC molecule present on an antigen presenting cell (APS) to a specific T cell receptor (TCR). Assembly of a trimolecular complex comprising the autoantigenic peptide, the MHC molecule and the TCR is required to trigger the T cell immune response. Described herein is a novel strategy to prevent or disrupt the assembly of the trimolecular complex and thus prevent the triggering of the autoimmune response. The strategy is based, in part, on generation of molecules that specifically target the autoantigenic peptide-MHC class II molecule complex and disrupt or prevent the assembly of the primary autoimmune trimolecular complex comprising the autoantigen, the class II MHC molecule, and the T cell receptor molecule implicated in the autoimmune disease. Accordingly, described herein are novel therapeutic compositions and methods for the treatment or prevention of autoimmune diseases, comprising molecules that specifically target the autoantigenic peptide-MHC class II molecule complex and prevent or disrupt the assembly of autoantigenic peptide-MHC class II molecule-TCR trimolecular complex.

The present inventors have successfully tested this strategy in the treatment of type 1 diabetes. Type 1 diabetes, an organ-specific autoimmune disease, is characterized by the production of autoantibodies that target the insulin-secreting pancreatic beta cells. The destruction of the beta cells is mainly due to the action of T cells. In most cases T cells can respond to an antigen only when the antigen is properly presented by an antigen presenting cell expressing the appropriate major histocompatibility complex (MHC) molecule. Thus, T cell immune response to an antigen requires recognition by the T cell receptor of the antigen coupled to a MHC molecule, and requires assembly of a tri-molecular complex comprising the antigen, the MHC molecule and the T cell receptor.

Data obtained from NOD (non-obese diabetic) mouse model indicate that insulin is a key or primary autoantigen in the development of type 1 diabetes (1-3). Initial cloning of T cells from islets of NOD mice led to the discovery that the native insulin B chain amino acids 9-23 having the sequence SHLVEALYLVCGERG (SEQ ID NO:1) ("B:9-23 peptide") is the dominant antigenic peptide epitope presented by the class II MHC molecule I-A. Mice lacking the native B:9-23 sequence fail to develop diabetes, and development of insulin autoantibodies and insulitis are markedly decreased (4). Restoring the native B:9-23 sequence with an islet transplant (but not bone marrow transplant) or peptide injection or a native proinsulin transgene, restores anti-insulin autoimmunity and generates CD4 T cells able to cause diabetes (5).

The major genetic determinant of islet autoimmunity and diabetes in man and animal models are genes within the major histocompatibility complex (6; 7), in particular class II MHC alleles (8-10). The NODs unique sequence of the MHC class II allele I-A (homologous to DQ8 (DQB1*0302) of man) and lack of expression of 1-E (shared with many standard mouse strains) are essential for the development of diabetes.

Figure 1B:
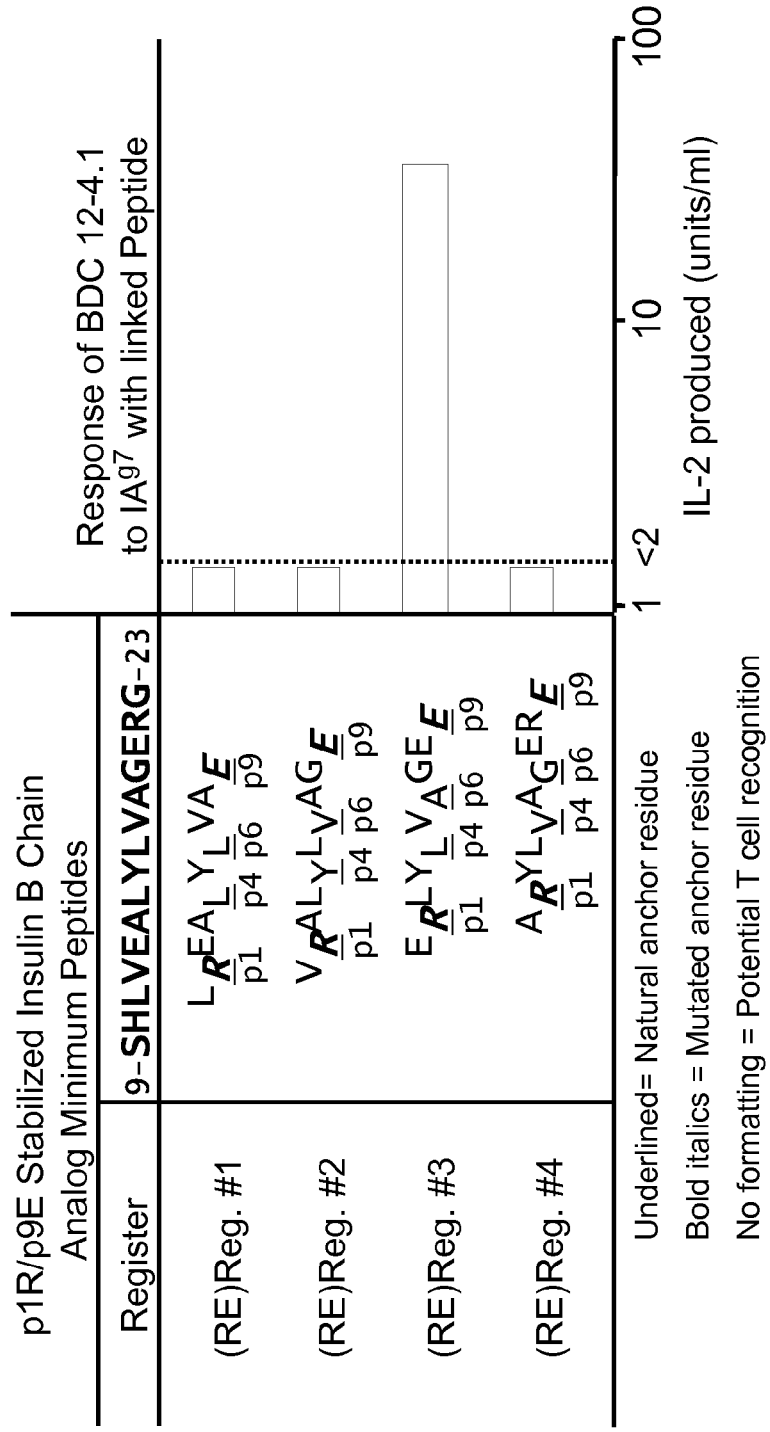
FIG. 1B shows the mouse insulin B-chain, B:9-23 CD4$^+$ T cell minimal peptide and its possible binding registers. Anchor residues are underlined; the mutated anchor residues (RE) for preventing register shifting are in bold italics and are underlined, while the remaining residues show the amino acids that can potentially contact the T cell antigen receptor. Registers 1, 2, and 4 all use anchor residues that are compatible with the IA$^{g7}$ peptide binding motif, while register 3 is a nonpreferred binding motif due to the arginine in the MHC P9 pocket.
Figure 1C:
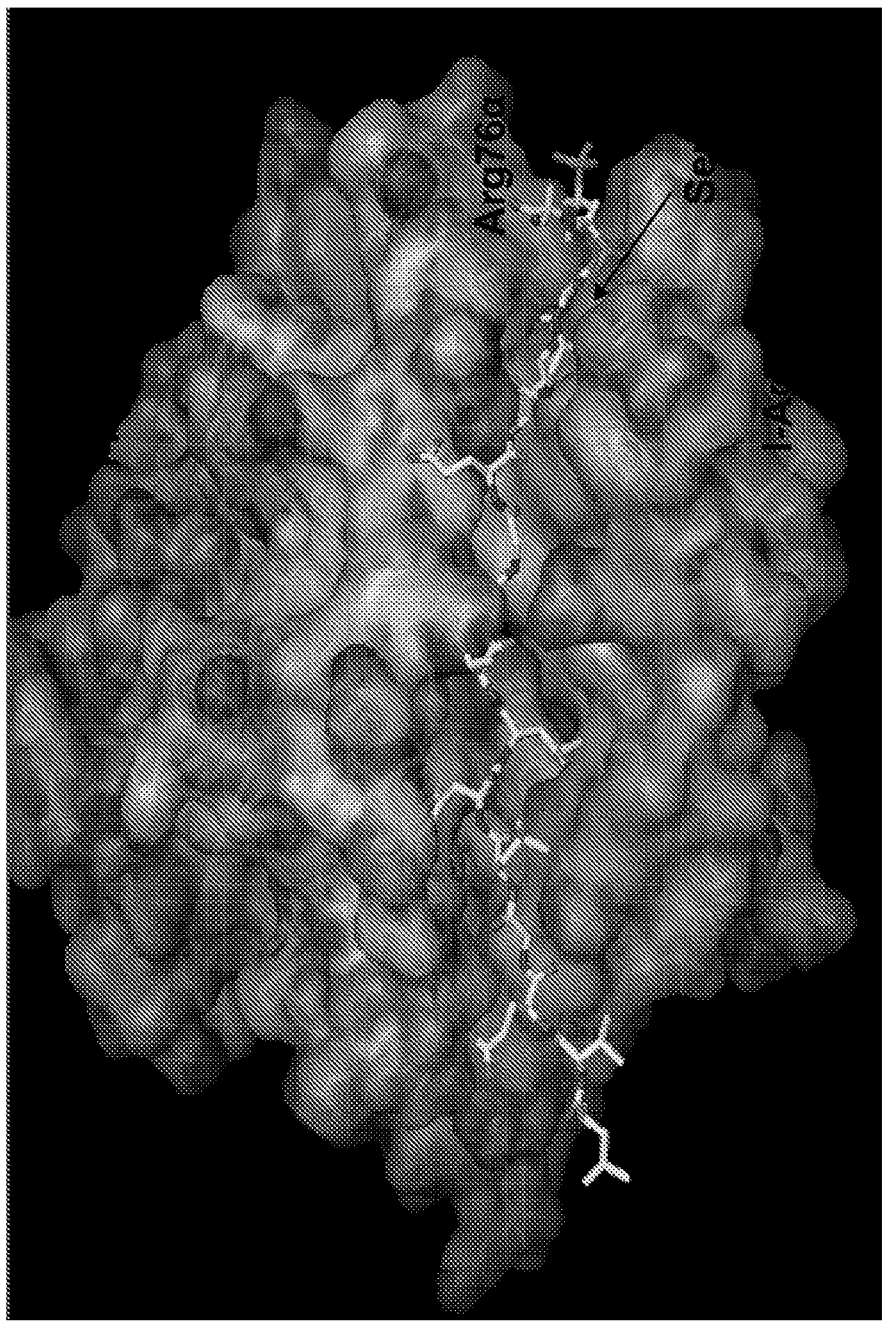
FIG. 1C shows the computer modeling of the 3-dimensional structure of IA$^{g7}$-B:9-23 in register 3 (abbreviated as B:12-22RE-Reg3).

The crystal structure of I-A$^{g7}$ with a bound peptide is available allowing modeling of binding of peptides to this molecule (11). There are multiple registers in which the B:9-23 peptide can bind to I-A$^{g7}$. FIG. 1B shows four registers of the peptide, while FIG. 1C depicts the I-A$^{g7}$ molecule linked with the peptide B:12-22RE(Reg3) having the sequence VERLYLVAGEE (SEQ ID NO:8).

There are alternative hypotheses as to why I-A$^{g7}$ (and DQB1*0302 (12)) is associated with islet autoimmunity. One hypothesis is that the molecule is a poor binder of peptides and potentially unstable (13; 14), and such instability or defective binding might limit negative selection of autoimmune T cells within the thymus. Another hypothesis is that I-A$^{g7}$ is critical for presentation of specific autoantigenic peptide(s) in the periphery (2; 15-17). The second hypothesis is supported by the observation that I-A alleles such as I-A$^k$ prevent NOD diabetes but enhance alternative autoimmune disorders, suggesting that class II alleles determine the specific organ targeted rather than general susceptibility to auto immunity (18; 19).

Finally recognition of the B9:23 epitope is dependent upon targeting of B:9-23 bound to I-A$^{g7}$ by a conserved "non-stringent" T cell receptor with germline encoded TRAY 5D-4*04 α chain sequence. Of the elements of α/β T cell receptors that vary (Vα, Nα, Jα; Vβ, Nβ, Dβ, Jβ) our preliminary data indicates that the Vα TRAY 5D-4*04 sequence (within multiple T cell receptors) is sufficient to engender anti-B:9-23/anti-insulin/anti-islet autoimmunity and diabetes, despite multiple different sequences of the other TCR elements. The present inventors have demonstrated that the conserved TRAV5D-4*04 containing α chain with endogenous TCRβ chains is able to induce insulin autoimmunity (20) and have produced T cell receptor hybridomas from such mice to study the molecular determinants of targeting B:9-23.

Thus, to trigger the autoimmune response in NOD mice requires the assembly of a trimolecular complex comprising I-A$^{g7}$ (class II MHC molecule), B9:23 (insulin autoantigenic peptide) and TRAV5D-4*04 (or related TRAYS-1 and TRAV10) containing T cell receptor (see FIG. 1A), which requires recognition of I-A$^{g7}$-B9:23 complex by the TRAV5D-4*04 (or related TRAV5-1 and TRAV10) containing TCR.

Accordingly, in some embodiments the present invention includes methods for treatment or prevention of type 1 diabetes comprising generation of antibodies that specifically bind to the I-A$^{g7}$-insulin B autoantigenic peptide such as B:9-23 covalently linked complex and prevent or disrupt the assembly of I-A$^{g7}$-B9:23-TCR complex or block binding of the I-A$^{g7}$-B9:23 to the TCR. Also described herein are therapeutic compositions for the prevention or treatment of type 1 diabetes.

While the data presented herein is related to the development of type 1 diabetes, one skilled in the art will readily appreciate that the overall strategy, as well as the methods and compositions described herein would apply to any autoimmune disease that involves a T cell response and recognition by the TCR of an autoantigenic peptide implicated in that disease presented by the appropriate MHC molecule.

In one embodiment, the present invention includes a therapeutic composition comprising a peptide linked to a class II MHC molecule for immunizing an animal so that the animal produces an antibody that has an inhibitory or preventive activity on an autoimmune disease in the animal. The peptide used in the present invention may be an autoantigenic peptide that is implicated in the development of that autoimmune disease. In some embodiments, the peptide may also include a modified version of the autoantigenic peptide such that it binds in a specific register of the MHC class II molecule and is reactive with the specific T cell receptor implicated in that autoimmune disease. Although the linkage between the peptide and the class II MHC molecule may be of any nature, to ensure tight linkage, the peptide is preferably covalently attached to the MHC molecule.

The therapeutic composition is administered to immunize the animal so that the animal produces an antibody that has an inhibitory or preventive activity on an autoimmune disease in the animal. The antibody produced in the animal selectively binds to the complex comprising the class II MHC molecule and the peptide. Without wishing to be bound by theory, it is expected that the antibody prevents the association of or disrupts the specific trimolecular complex implicated in the autoimmune disease comprising the class II MHC molecule, the autoantigen and the T cell receptor and thus prevents the development of or inhibits the autoimmune disease.

The therapeutic composition of the present invention can be used in the treatment of any autoimmune disease that involves a T cell response. Examples include, without limitation, Hashimoto's thyroiditis, Graves' disease, pernicious anemia, Addison's disease, chronic active hepatitis, myasthenia gravis, rheumatoid arthritis, multiple sclerosis and lupus. In preferred embodiments the autoimmune disease is type 1 diabetes, pre-diabetes of type 1A, and Latent Autoimmune Diabetes in Adults (LADA). In a particularly preferred embodiment the autoimmune disease is type 1 diabetes.

In one aspect, the autoimmune disease is type 1 diabetes, the autoantigen is insulin, the class II MHC molecule is I-A$^{g7}$ (or its homolog), and the TCR is a TCR containing an α chain selected from the group consisting of TRAV5D-4, TRAV5-1 and TRAV10 (or its homolog). As explained above, B:9-23 peptide having the amino acid sequence SHLVEALYLVCGERG (SEQ ID NO:1) is the dominant antigenic peptide epitope presented by the class II MHC molecule I-A$^{g7}$ in the development of type 1 diabetes. Accordingly, in some embodiments the therapeutic composition may comprise the peptide B:9-23 tethered to the I-A$^{g7}$ molecule. In some embodiments, the therapeutic composition may comprise truncated or modified versions of B:9-23, including without limitation, peptides B:12-23 having the amino acid sequence VEALYLVCGERG (SEQ ID NO:2), B:12-22 having the amino acid sequence VEALYLVCGER (SEQ ID NO:3), or B:13-22 having the amino acid sequence EALYLVCGER (SEQ ID NO:9). In some embodiments, A may be substituted for C in the native sequence. Additionally, the therapeutic composition may comprise different registers of the peptide such as (RE)Reg1 having the amino acid sequence LREALYLVAE (SEQ ID NO:4), (RE)Reg2 having the amino acid sequence VRALYLVAGE (SEQ ID NO:5), (RE)Reg3 having the amino acid sequence ERLYLVAGEE (SEQ ID NO:6) or (RE)Reg4 having the amino acid sequence ARYLVAGERE (SEQ ID NO:7), or B:12-22RE Reg.3 comprising SEQ ID NO:8 (VERLYLVAGEE) that are capable of binding to I-A$^{g7}$ and being recognized by the specific TCR.

In some embodiments, the therapeutic composition is a vaccine. The therapeutic composition or vaccine of the invention can further include any other compounds that are useful for protecting a subject from a particular disease or condition, including an infection by a pathogen, or any compounds that treat or ameliorate any symptom of such an infection. The therapeutic compositions of the invention can further include a pharmaceutically acceptable carrier. Such a carrier can include, but is not limited to, an adjuvant, an excipient, or carrier. According to the present invention, adjuvants are typically substances that generally enhance the immune response of an animal to a specific antigen. Suitable adjuvants include, but are not limited to, incomplete Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax adjuvant (CytRx™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark). Adjuvants are not required in the present invention, but their use is not excluded. Carriers are typically compounds that increase the half-life of a therapeutic composition in the treated animal. Suitable carriers include, but are not limited to, polymeric controlled release formulations, biodegradable implants, liposomes, oils, esters, and glycols. Compositions and vaccines of the present invention can also contain one or more pharmaceutically acceptable excipients. As used herein, a pharmaceutically acceptable excipient refers to any substance suitable for delivering a composition useful in a method of the present invention to a suitable in vivo or ex vivo site. Preferred pharmaceutically acceptable excipients are capable of maintaining a composition in a form that, upon arrival of the composition at a target cell, tissue, or site in the body, the composition is capable of eliciting an immune response at the target site (noting that the target site can be systemic). Suitable excipients of the present invention include excipients or formularies that transport, but do not specifically target the vaccine to a site (also referred to herein as non-targeting carriers). Examples of pharmaceutically acceptable excipients include, but are not limited to water, saline, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Auxiliary substances can also include preservatives. Stabilizers, such as trehalose, glycine, sorbitol, lactose or monosodium glutamate (MSG), can be added to stabilize the vaccine formulation against a variety of conditions, such as temperature variations or a freeze-drying process. Compositions may also include a suspending fluid such as sterile water or saline (preferably buffered).

In some embodiments of the present invention, the therapeutic composition or vaccine can also include biological response modifier compounds, although such modifiers are not necessary to achieve a robust immune response according to the invention. For example, the vaccine or composition of the invention can be administered in conjunction with at least one biological response modifier. Biological response modifiers include compounds that can modulate immune responses, which may be referred to as immunomodulatory compounds. Certain biological response modifiers can stimulate a protective immune response whereas others can suppress a harmful immune response. Suitable biological response modifiers include cytokines, hormones, lipidic derivatives, small molecule drugs and other growth modulators, such as, but not limited to, interleukin 2 (IL-2), interleukin 4 (IL-4), interleukin 10 (IL-10), interleukin 12 (IL-12), interferon gamma (IFN-gamma) insulin-like growth factor I (IGF-I), transforming growth factor beta (TGF-β) steroids, prostaglandins and leukotrienes. The ability of a yeast vehicle to express (i.e., produce), and possibly secrete, IL-2, IL-12 and/or IFN-gamma preferentially enhances cell-mediated immunity, whereas the ability of a yeast vehicle to express, and possibly secrete, IL-4, IL-5 and/or IL-10 preferentially enhances humoral immunity. Other suitable biological response modifiers include, but are not limited to, anti-CTLA-4 antibody (e.g., to release anergic T cells); T cell co-stimulators (e.g., anti-CD137, anti-CD28, anti-CD40); alemtuzumab (e.g., CamPath®), denileukin diftitox (e.g., ONTAK®), anti-CD4, anti-CD25, anti-PD-1, anti-PD-L1, anti-PD-L2 or agents that block FOXP3 (e.g., to abrogate the activity/kill CD4+/CD25+ T regulatory cells); Flt3 ligand, imiquimod (Aldara™), GM-CSF, sargramostim (Leukine®), Toll-like receptor (TLR)-7 agonists, or TLR-9 agonists (e.g., agents that increase the number of, or increase the activation state, of dendritic cells, macrophages and other professional antigen-presenting cells). Such biological response modifiers are well known in the art and are publicly available.

The present invention includes the delivery of the therapeutic composition or vaccine of the invention to an animal. The administration process can be performed ex vivo or in vivo. Ex vivo administration refers to performing part of the regulatory step outside of the patient, such as administering the therapeutic composition of the present invention to a population of cells removed from a patient under conditions such that the composition is administered to the cells, and returning the cells to the patient. The therapeutic composition of the present invention can be returned to a patient, or administered to a patient, by any suitable mode of administration.

The preferred routes of administration will be apparent to those of skill in the art. Methods of administration include, but are not limited to, parenteral, intravenous administration, intraperitoneal administration, intramuscular administration, intranodal administration, intracoronary administration, intraarterial administration (e.g., into a carotid artery), subcutaneous administration, transcutaneous administration, transdermal delivery, intratracheal administration, intraarticular administration, intraventricular administration, inhalation (e.g., aerosol), intracranial, intraspinal, intraocular, aural, intranasal, oral, pulmonary administration, impregnation of a catheter, and direct injection into a tissue. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., *Proc. Natl. Acad. Sci. USA* 189: 11277-11281, 1992, which is incorporated herein by reference in its entirety). For example, in one embodiment, a composition or vaccine of the invention can be formulated into a composition suitable for nebulized delivery using a suitable inhalation device or nebulizer. Oral delivery can include solids and liquids that can be taken through the mouth. Particularly preferred routes of administration include: parenteral, intravenous, subcutaneous, oral and nasal and transcutaneous.

According to the present invention, an effective administration protocol comprises suitable dose parameters and modes of administration that result in elicitation of an appropriate immune response in an animal. Effective dose parameters can be determined using methods standard in the art for a particular disease. Such methods include, for example, determination of survival rates, side effects (i.e., toxicity) and progression or regression of disease.

The therapeutic composition of the present invention can be stored in a dried or lyophilized form or in solution. Prior to administration, the composition may be re-suspended or diluted in a suitable diluent such as sterile water, saline, isotonic buffered saline (e.g. phosphate buffered to physiological pH), or other suitable diluent.

The present invention further contemplates kits comprising the therapeutic composition or vaccine. In one aspect, this kit can additionally include preparations to be used in a priming or boosting vaccine strategy, (to be administered concurrently or sequentially, in prime/boost strategies, and the like, as described herein). Kits may also include excipients, carriers and/or adjuvants as described herein. A set of instructions for use can be included with any kit of the invention.

In one embodiment, the present invention comprises an isolated antibody having an inhibitory or preventive activity on an autoimmune disease in an animal, wherein the antibody specifically binds to a complex comprising a class II MHC molecule and an autoantigenic peptide implicated in that disease. This is often termed passive humoral immunotherapy in contrast to vaccination. The isolated antibody of the present invention specifically targets prevents or disrupts the assembly of a trimolecular complex comprising a class II MHC molecule, an autoantigen and a T cell receptor. In preferred embodiments, the autoimmune disease is type 1 diabetes and the class II MHC molecule is I-Ag7 and the peptide is selected from the group consisting of B9:23 comprising SEQ ID NO:1 (SHLVEALYLVCGERG), B12:23 comprising SEQ ID NO:2 (VEALYLVCGERG), B12:22 comprising SEQ ID NO:3 (VEALYLVCGER), B:13-22 comprising SEQ ID NO:9 (EALYLVCGER), B12:22 RE(Reg3) comprising SEQ ID NO:8 (VERLYLVAGEE), (RE)Reg.1 comprising SEQ ID NO:4 (LREALYLVAE), (RE)Reg.2 comprising SEQ ID NO:5 (VRALYLVAGE), (RE)Reg.3 comprising SEQ ID NO:6 (ERLYLVAGEE), (RE)Reg.4 comprising SEQ ID NO:7 (ARYLVAGERE), and a homolog thereof. In some embodiments, the antibody is human or humanized. In some embodiments, the antibody comprises a Fab, Fab', F(ab')2, or scFv fragment. In some embodiments, the antibody is monoclonal.

In a further embodiment, the present invention includes a method for preventing or treating an autoimmune disease comprising administering to a subject in need thereof an effective amount of a therapeutic composition comprising an isolated antibody that specifically binds to a complex comprising a class II MHC molecule and an autoantigenic peptide implicated in the autoimmune disease. In another embodiment, the present invention includes a method for preventing or treating an autoimmune disease comprising immunizing a subject with an effective amount of a therapeutic composition comprising a peptide, wherein the peptide is an autoantigenic peptide implicated in the autoimmune disease, and immunization leads to production of an antibody that specifically binds to a complex comprising a class II MHC molecule and the peptide.

In another embodiment, the present invention includes a production method of an antibody having a therapeutic effect in an autoimmune disease, the method comprising: an immunization step of immunizing a non-human animal with an autoantigenic peptide implicated in the autoimmune disease attached to a class II MHC molecule; a hybridoma production step of fusing an antibody producing cell taken out from the immunized non-human animal with an immortalized cell so as to obtain a hybridoma; a hybridoma selection step of selecting a hybridoma producing an antibody having a binding property to the said peptide; and an antibody separation step for separating an antibody expressed by the selected hybridoma.

Generally speaking, an antibody molecule comprises two types of chains. One type of chain is referred to as the heavy or H chain and the other is referred to as the light or L chain. The two chains are present in an equimolar ratio, with each antibody molecule typically having two H chains and two L chains. The two H chains are linked together by disulfide bonds and each H chain is linked to a L chain by a disulfide bond. There are only two types of L chains referred to as lambda ($\lambda$) and kappa ($\kappa$) chains. In contrast, there are five major H chain classes referred to as isotypes. The five classes include immunoglobulin M (IgM or $\mu$), immunoglobulin D (IgD or $\delta$), immunoglobulin G (IgG or $\lambda$), immunoglobulin A (IgA or $\alpha$), and immunoglobulin E (IgE or $\epsilon$). The distinctive characteristics between such isotypes are defined by the constant domain of the immunoglobulin and are discussed in detail below. Human immunoglobulin molecules comprise nine isotypes, IgM, IgD, IgE, four subclasses of IgG including IgG1 ($\gamma$1), IgG2 ($\gamma$2), IgG3 ($\gamma$3) and IgG4 ($\gamma$4), and two subclasses of IgA including IgA1 ($\alpha$1) and IgA2 ($\alpha$2). Each H or L chain of an immunoglobulin molecule comprises two regions referred to as L chain variable domains ($V_L$ domains) and L chain constant domains ($C_L$ domains), and H chain variable domains ($V_H$ domains) and H chain constant domains ($C_H$ domains). A complete $C_H$ domain comprises three sub-domains ($C_{H1}$, $C_{H2}$, $C_{H3}$) and a hinge region. Together, one H chain and one L chain can faun an arm of an immunoglobulin molecule having an immunoglobulin variable region. A complete immunoglobulin molecule comprises two associated (e.g., di-sulfide linked) arms. Thus, each arm of a whole immunoglobulin comprises a $V_{H+L}$ region, and a $C_{H+L}$ region. As used herein, the term "variable region" or "V region" refers to a $V_{H+L}$ region (also known as an Fv fragment), a $V_L$ region or a $V_H$ region. Also as used herein, the term "constant region" or "C region" refers to a $C_{H+L}$ region, a $C_L$ region or a $C_H$ region. Single chain antibodies binding to the same complex are not excluded.

Limited digestion of an immunoglobulin with a protease may produce two fragments. An antigen binding fragment is referred to as an Fab, an Fab', or an F(ab')$_2$ fragment. A fragment lacking the ability to bind to antigen is referred to as an Fc fragment. A Fab fragment comprises one arm of an immunoglobulin molecule containing a L chain ($V_L$+$C_L$ domains) paired with the $V_H$ region and a portion of the $C_H$ region (CH1 domain). A Fab' fragment corresponds to a Fab fragment with part of the hinge region attached to the CH1 domain. A F(ab')2 fragment corresponds to two Fab' fragments that are normally covalently linked to each other through a di-sulfide bond, typically in the hinge regions. The CH domain defines the isotype of an immunoglobulin and confers different functional characteristics depending upon the isotype. For example, $\mu$ constant regions enable the formation of pentameric aggregates of IgM molecules and $\alpha$ constant regions enable the formation of dimers.

The antigen specificity of an immunoglobulin molecule is conferred by the amino acid sequence of a variable, or V, region. As such, V regions of different immunoglobulin molecules can vary significantly depending upon their antigen specificity. Certain portions of a V region are more conserved than others and are referred to as framework regions (FW regions). In contrast, certain portions of a V region are highly variable and are designated hypervariable regions. When the $V_L$ and $V_H$ domains pair in an immunoglobulin molecule, the hypervariable regions from each domain associate and create hypervariable loops that form the antigen binding sites. Thus, the hypervariable loops determine the specificity of an immunoglobulin and are termed complementarity-determining regions (CDRs) because their surfaces are complementary to antigens. Further variability of V regions is conferred by combinatorial variability of gene segments that encode an immunoglobulin V region. Immunoglobulin genes comprise multiple germline gene segments which somatically rearrange to form a rearranged immunoglobulin gene that encodes an immunoglobulin molecule. $V_L$ regions are encoded by a L chain V gene segment and J gene segment (joining segment). $V_H$ regions are encoded by a H chain V gene segment, D gene segment (diversity segment) and J gene segment (joining segment).

Both a L chain and H chain V gene segment contain three regions of substantial amino acid sequence variability. Such regions are referred to as L chain CDR1, CDR2 and CDR3, and H chain CDR1, CDR2 and CDR3, respectively. The length of an L chain CDR1 can vary substantially between different $V_L$ regions. For example, the length of CDR1 can vary from about 7 amino acids to about 17 amino acids. In contrast, the lengths of L chain CDR2 and CDR3 typically do not vary between different $V_L$ regions. The length of a H chain CDR3 can vary substantially between different $V_H$ regions. For example, the length of CDR3 can vary from about 1 amino acid to about 20 amino acids. Each H and L chain CDR region is flanked by FW regions.

In one embodiment, the antibodies of the present invention that are particularly useful in human patients are humanized antibodies. Humanized antibodies are molecules having an antigen binding site derived from an immunoglobulin from a non-human species, the remaining immunoglobulin-derived parts of the molecule being derived from a human immunoglobulin. The antigen binding site may comprise either complete variable regions fused onto human constant domains or only the complementarity determining regions (CDRs) grafted onto appropriate human framework regions in the variable domains. Humanized antibodies can be produced, for example, by modeling the antibody variable domains, and producing the antibodies using genetic engineering techniques, such as CDR grafting (described below). A description of various techniques for the production of humanized antibodies is found, for example, in Morrison et al. (1984) Proc. Natl. Acad. Sci. USA 81:6851-55; Whittle et al. (1987) Prot. Eng. 1:499-505; Co et al. (1990) J. Immunol. 148:1149-1154; Co et al. (1992) Proc. Natl. Acad. Sci. USA 88:2869-2873; Carter et al. (1992) Proc. Natl. Acad. Sci. 89:4285-4289; Routledge et al. (1991) Eur. J. Immunol. 21:2717-2725 and PCT Patent Publication Nos. WO 91/09967; WO 91/09968 and WO 92/113831.

In some embodiments, the antibody of the present invention comprises an Fab, Fab', F(ab')2, or scFv fragment. The terms Fab, Fab', F(ab')2 have been described above. A single chain variable fragment (scFv) is a fusion of the variable regions of the heavy and light chains of immunoglobulins, linked together with a short linker, usually serine or glycine. This chimeric molecule retains the specificity of the original immunoglobulin, despite removal of the constant regions and the introduction of a linker peptide. A scFv fragment can be created directly from subcloned heavy and light chains derived from a hybridoma.

Isolated antibodies of the present invention can include serum containing such antibodies, or antibodies that have been purified to varying degrees. Whole antibodies of the present invention can be polyclonal or monoclonal. Alternatively, functional equivalents of whole antibodies, such as antigen binding fragments in which one or more antibody domains are truncated or absent (e.g., Fv, Fab, Fab', or F(ab)$_2$ fragments), as well as genetically-engineered antibodies or antigen binding fragments thereof, including single chain antibodies, humanized antibodies (discussed above), antibodies that can bind to more than one epitope (e.g., bi-specific antibodies), or antibodies that can bind to one or more different antigens (e.g., bi- or multi-specific antibodies), may also be employed in the invention.

Generally, in the production of an antibody, a suitable experimental animal, such as, for example, but not limited to, a rabbit, a sheep, a hamster, a guinea pig, a mouse, a rat, or a chicken, is exposed to an antigen against which an antibody is desired. Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies. Such serum is useful as a reagent. Polyclonal antibodies can be further purified from the serum by, for example, treating the serum with ammonium sulfate.

In some embodiments, the antibody of the present invention is monoclonal. Monoclonal antibodies may be produced according to the methodology of Kohler and Milstein (Nature 256:495-497, 1975). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen.

A preferred method to produce antibodies of the present invention includes (a) administering to an animal an effective amount of a protein or peptide (e.g., an autoantigenic peptide linked to a class II MHC molecule) to produce the antibodies and (b) recovering the antibodies. In another method, antibodies of the present invention are produced recombinantly. For example, once a cell line, for example a hybridoma, expressing an antibody according to the invention has been obtained, it is possible to clone therefrom the cDNA and to identify the variable region genes encoding the desired antibody, including the sequences encoding the CDRs. From here, antibodies and antigen binding fragments according to the invention may be obtained by preparing one or more replicable expression vectors containing at least the DNA sequence encoding the variable domain of the antibody heavy or light chain and optionally other DNA sequences encoding remaining portions of the heavy and/or light chains as desired, and transforming/transfecting an appropriate host cell, in which production of the antibody will occur. Suitable expression hosts include bacteria, (for example, an *E. coli* strain), fungi, (in particular yeasts, e.g. members of the genera *Pichia, Saccharomyces,* or *Kluyveromyces,*) and mammalian cell lines, e.g. a non-producing myeloma cell line, such as a mouse NSO line, or CHO cells. In order to obtain efficient transcription and translation, the DNA sequence in each vector should include appropriate regulatory sequences, particularly a promoter and leader sequence operably linked to the variable domain sequence. Particular methods for producing antibodies in this way are generally well known and routinely used. For example, basic molecular biology procedures are described by Maniatis et al. (Molecular Cloning, Cold Spring Harbor Laboratory, New York, 1989); DNA sequencing can be performed as described in Sanger et al. (PNAS 74, 5463, (1977)) and the Amersham International plc sequencing handbook; and site directed mutagenesis can be carried out according to the method of Kramer et al. (Nucl. Acids Res. 12, 9441, (1984)) and the Anglian Biotechnology Ltd. handbook. Additionally, there are numerous publications, including patent specifications, detailing techniques suitable for the preparation of antibodies by manipulation of DNA, creation of expression vectors and transformation of appropriate cells, for example as reviewed by Mountain A and Adair, J R in Biotechnology and Genetic Engineering Reviews (ed. Tombs, M P, 10, Chapter 1, 1992, Intercept, Andover, UK) and in the aforementioned European Patent Applications.

In some embodiments the antibody of the present invention is administered to the animal by passive infusion. The antibody may be administered along with a pharmaceutically acceptable carrier. Preferred pharmaceutically acceptable carriers are capable of maintaining the antibody in a form that, upon arrival of the antibody at the cell target in a patient, the antibody is capable of selectively binding to the target and prevent the assembly of or disrupt the trimolecular complex. Suitable excipients of the present invention include excipients or formularies that transport or help transport, but do not specifically target a composition to a cell (also referred to herein as non-targeting carriers). Examples of pharmaceutically acceptable excipients include, but are not limited to, water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol. Formulations of the present invention can be sterilized by conventional methods and/or lyophilized.

One type of pharmaceutically acceptable carrier includes a controlled release formulation that is capable of slowly releasing a formulation of the present invention into the animal. As used herein, a controlled release formulation comprises an antibody of the present invention in a controlled release vehicle. Suitable controlled release vehicles include, but are not limited to, biocompatible polymers, other polymeric matrices, microcapsules, microparticles, liposomes, or liposheres. Other suitable carriers include any carrier that can be bound to or incorporated with the antibody that extends that half-life of the antibody to be delivered. Such a carrier can include any suitable protein carrier or even a fusion segment that extends the half-life of an antibody when delivered in vivo.

According to the present invention, an effective administration protocol (i.e., administering the isolated antibody in an effective manner) comprises suitable dose parameters and modes of administration that result in elicitation of the appropriate response in the animal having the autoimmune disease, or that is at risk of contracting such autoimmune disease, preferably so that the animal is protected from the disease. Effective dose amounts depend upon successful blocking of T cell responses to the auto-antigen implicated in the disease and can be determined using methods standard in the art for the particular disease. Such methods include, for example, determination of survival rates, side effects (i.e., toxicity) and progression or regression of the disease. In various embodiments, the antibody of the present invention may be administered to the animal in an amount ranging from about 1 µg/kg to about 500,000 µg/kg, 10 µg/kg to about 100,000 µg/kg and from about 50 µg/kg to about 50,000 µg/kg weight of the animal. In preferred embodiments, the antibody of the present invention may be administered to the animal in an amount ranging from about 100 µg/kg to about 10,000 µg/kg weight of the animal.

General Techniques

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, *Methods of Enzymology*, Vol. 194, Guthrie et al., eds., Cold Spring Harbor Laboratory Press (1990); *Biology and activities of yeasts*, Skinner, et al., eds., Academic Press (1980); *Methods in yeast genetics: a laboratory course manual*, Rose et al., Cold Spring Harbor Laboratory Press (1990); *The Yeast Saccharomyces: Cell Cycle and Cell Biology*, Pringle et al., eds., Cold Spring Harbor Laboratory Press (1997); *The Yeast Saccharomyces: Gene Expression*, Jones et al., eds., Cold Spring Harbor Laboratory Press (1993); *The Yeast Saccharomyces: Genome Dynamics, Protein Synthesis, and Energetics*, Broach et al., eds., Cold Spring Harbor Laboratory Press (1992); *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994); Harlow and Lane (1988) *Antibodies, A Laboratory Manual*, Cold Spring Harbor Publications, New York; Harlow and Lane (1999) *Using Antibodies: A Laboratory Manual* Cold Spring Harbor Laboratory Press, Cold Spring Harbor, N.Y. (jointly referred to herein as "Harlow and Lane"), Beaucage et al. eds., *Current Protocols in Nucleic Acid Chemistry* John Wiley & Sons, Inc., New York, 2000); *Casarett and Doull's Toxicology The Basic Science of Poisons*, C. Klaassen, ed., 6th edition (2001), and *Vaccines*, S. Plotkin and W. Orenstein, eds., $3^{rd}$ edition (1999).

General Definitions

"Immunization" or "Vaccination" refers to the elicitation (induction) of an immune response against an antigen or immunogenic portion thereof, as a result of administration of the antigen, alone or together with an adjuvant. Vaccination preferably results in a protective or therapeutic effect, wherein subsequent exposure to the antigen (or a source of the antigen) elicits an immune response against the antigen (or source) that reduces or prevents a disease or condition in the animal. The concept of vaccination is well known in the art. The immune response that is elicited by administration of a composition (vaccine) of the present invention can be any detectable change in any facet of the immune response (e.g., cell-mediated response, humoral response, cytokine production), as compared to in the absence of the administration of the composition.

A "humoral immune response" refers generally to antibody production, and to all of the processes that accompany antibody production, including, but not limited to, B lymphocyte (B cell) activation, affinitiy maturation, differentiation into plasma cells, and memory B cell generation, germinal center formation and isotype switching, and T helper cell activation, signaling, and cytokine production, as well as effector functions of antibodies, which include neutralization, classical complement activation, and opsonization.

A "cell-mediated" immune response (which may be used interchangeably anywhere herein with the term "cellular" immune response) refers generally to the response to an antigen of immune cells including T lymphocytes (including cytotoxic T lymphocytes (CTL)), dendritic cells, macrophages, and natural killer cells, and to all of the processes that accompany such responses, including, but not limited to, activation and proliferation of these cells, CTL effector functions, cytokine production that influences the function of other cells involved in adaptive immune responses and innate immune responses, and memory T cell generation.

According to the present invention, the general use herein of the term "antigen" refers: to any portion of a protein (peptide, partial protein, full-length protein), wherein the protein is naturally occurring or synthetically derived, to a cellular composition (whole cell, cell lysate or disrupted cells), to an organism (whole organism, lysate or disrupted cells) or to a carbohydrate (such as those expressed on cancer cells), or other molecule, or a portion thereof. An antigen elicits an antigen-specific immune response (e.g., a humoral and/or a cell-mediated immune response) against the same or similar antigens that are encountered within the cells and tissues of an individual to which the antigen is administered.

An epitope is defined herein as a single immunogenic site within a given antigen that is sufficient to elicit an immune response. Epitopes can be linear sequence or conformational epitopes (conserved binding regions). An antigen can be as small as a single epitope, or larger, and can include multiple epitopes. As such, the size of an antigen can be as small as about 5-12 amino acids (e.g., a peptide) and as large as: a full length protein, including a multimer and fusion proteins, chimeric proteins, whole cells, whole microorganisms, or portions thereof (e.g., lysates of whole cells or extracts of microorganisms).

According to the present invention, the phrase "selectively binds to" refers to the ability of an antibody, antigen-binding fragment or binding partner of the present invention to preferentially bind to specified proteins. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen-binding fragment thereof in the absence of the antigen is considered to be background. Binding can be measured using a variety of methods standard in the art including enzyme immunoassays (e.g., ELISA), immunoblot assays, etc.).

An "animal" is a vertebrate, preferably a mammal, more preferably a human. Mammals include, but are not limited to, farm animals, sport animals, pets, primates, mice and rats. The term "animal" can be used interchangeably with the term "subject" or "patient."

The phrase "selectively binds to" refers to the ability of an antibody to preferentially bind to specified proteins, wherein the level of binding, as measured by any standard assay (e.g., an immunoassay), is statistically significantly higher than the background control for the assay. Binding can be measured using a variety of methods standard in the art including enzyme immunoassays (e.g., ELISA), immunoblot assays, etc.).

Reference to an isolated protein or peptide in the present invention includes full-length proteins, fusion proteins, or any fragment, domain, or homolog of such proteins. An isolated protein, according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified.

As used herein, the term "homolog" is used to refer to a protein or peptide which differs from the protein or peptide (i.e., the "prototype" protein) by one or more minor modifications or mutations to the protein or peptide, but which maintains the overall basic protein and side chain structure of the protein or peptide form (i.e., such that the homolog is identifiable as being related to the protein peptide). Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, farnesylation, geranyl geranylation, glycosylation, carboxymethylation, phosphorylation, acetylation, myristoylation, prenylation, palmitation, and/or amidation. It is noted that homologs can include synthetically produced homologs, naturally occurring allelic variants of a given protein or domain, or homologous sequences from organisms other than the organism from which the reference sequence was derived. Homologs can be the result of natural allelic variation or natural mutation. Homologs can be produced using techniques known in the art for the production of proteins including, but not limited to, direct modifications to the isolated, or synthesized naturally occurring protein, direct protein synthesis, or modifications to the nucleic acid sequence encoding the protein using, for example, classic or recombinant DNA techniques to effect random or targeted mutagenesis.

A homolog of a given protein may comprise, consist essentially of, or consist of, an amino acid sequence that is at least about 45%, or at least about 50%, or at least about 55%, or at least about 60%, or at least about 65%, or at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 45% and 99%, in whole integer increments), to the amino acid sequence of the reference protein. In one embodiment, the homolog comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the naturally occurring amino acid sequence of the reference protein.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

Conservative substitutions typically include substitutions within the following groups: glycine and alanine; valine, isoleucine and leucine; aspartic acid, glutamic acid, asparagine, and glutamine; serine and threonine; lysine and arginine; and phenylalanine and tyrosine. Substitutions may also be made on the basis of conserved hydrophobicity or hydrophilicity (Kyte and Doolittle, J. Mol. Biol. 157:105 (1982)), or on the basis of the ability to assume similar polypeptide secondary structure (Chou and Fasman, Adv. Enzymol. 47: 45 (1978)), or tertiary or quaternary structures.

The following examples are provided for illustrative purposes, and are not intended to limit the scope of the invention as claimed herein. Any variations which occur to the skilled artisan are intended to fall within the scope of the present invention. All references cited in the present application are incorporated by reference herein.

EXAMPLES

Example 1

This example illustrates that the I-A$^{g7}$-insulin autoantigenic peptide complex is able to stimulate a T cell immune response in vitro.

The autoantigenic peptide B:12-22RE(Reg3) having an amino acid sequence VERLYLVCGEE (SEQ ID NO:8) (also referred to as B:12-22RE or B:12-22Reg3) was covalently tethered to the beta chain of I-A$^{g7}$ and fixed in the specific register of I-A$^{g7}$ to be targeted by the pathogenic T cell receptor. Similarly, Hen Egg Lysozyme 11-23 having an amino acid sequence MKRHGLDNYRGYG (SEQ ID NO:10) ("HEL 11-23) was covalently attached to the I-A$^{g7}$ to provide the I-A$^{g7}$-HEL11-23 control complex.

Taking advantage of NFAT regulation of both LacZ and IL-2 genes, MHC-antigenic peptide complex-induced IL-2 production can be estimated by measuring LacZ activity in BWZ.36 derived T cell hybridomas by using chlorophenol red-P-D-galactopyranoside (CPRG) as the LacZ substrate. 96-well plates (flat bottom) were coated with I-A$^{g7}$-B:12-22RE-Reg3 complex or the control I-A$^{g7}$-HEL11-23 at 4° C. for overnight. The plates were washed three times with 200 µl PBS, after which 20,000 cells (BDC12-4.1 or BDC12-4.4 hybridomas) were loaded into each plate. The BDC12-4.1 and BDC12-4.4 clones were isolated from pancreatic lymph node cells of non-diabetic NOD mice; both of these cells recognize the B:9-23 peptide. After overnight incubation, cells were washed with PBS to remove the media which may interfere with absorbance reading and 100 µl of CPRG reagent (91 mg/L CPRG, 0.125% NP-40, 1 mM MgCl$_2$ in 10 mM phosphate buffer) was added. This causes cell lysis and intracellular LacZ is released into the supernatant. Cleavage of CPRG by LacZ resulted in production of chlorophenol red. The cells were lysed (4 hours at 37° C.) and absorbance was recorded in duplicate for one second per well at 575 nm and the reference wavelength of 655 nm.

Figure 2:
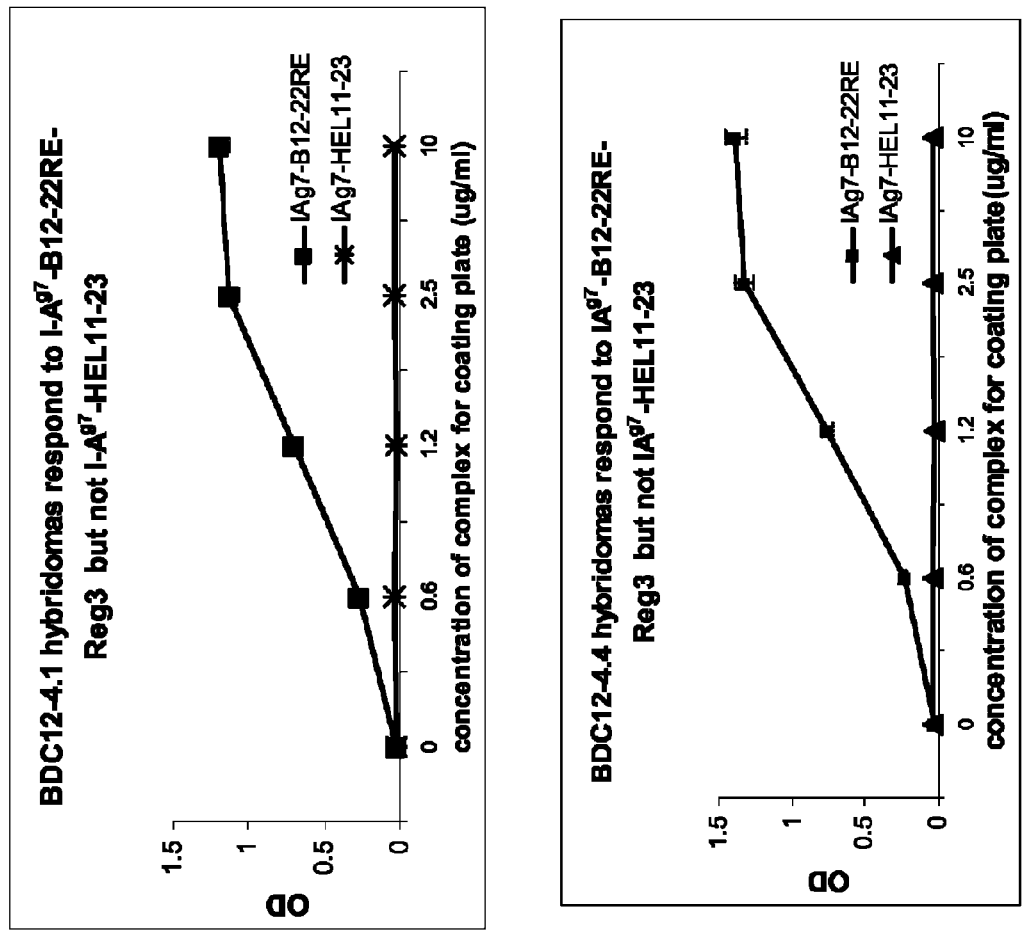
FIG. 2 graphically represents that IA$^{g7}$-B:12-22RE-Reg3 complex stimulates both BDC12-4.1 and BDC12-4.4 hybridoma cells, but the control IA$^{g7}$-HEL11-23 does not stimulate these cells.

As shown in FIG. 2, the plate bound I-A$^{g7}$-B:12-22RE-Reg3 complex stimulated both BDC12-4.1 and BDC12-4.4 hybridoma cells. However, I-A$^{g7}$-HEL11-23 did not stimulate the same cells.

Example 2

This example illustrates that the I-A$^{g7}$-insulin autoantigenic peptide complex specifically stimulates an immune response in cells expressing TRAV5D-4*04 TCR.

As explained above in Example 1, 96-well plates were coated with the I-A$^{g7}$-B:12-22RE-Reg3 complex or I-A$^{g7}$-HEL11-23 as control at 4° C. for overnight; plates were washed three times with PBS; and 20,000 cells (BDC12-4.1 or BDC12-4.4 or BDC2.5 hybridoma cells) were loaded into coated plates. BDC12-4.1 and BDC12-4.4 cells express the TRAV5D-4*04 containing TCR and recognize the B:9-23 peptide, whereas the BDC2.5 hybridoma cells do not express this TCR and recognize the non-insulin islet antigen HRPI-RM, not the insulin B:9-23 peptide. After overnight incubation, cells were washed and lysed and absorbance recorded in duplicate wells as described in Example 1.

Figure 3:
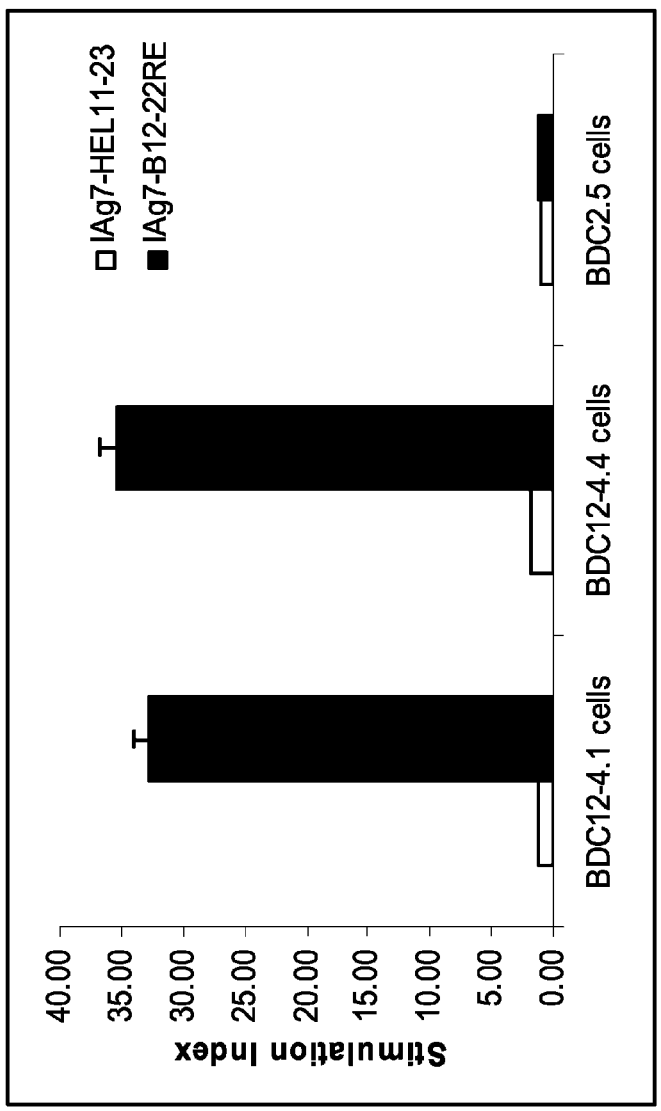
FIG. 3 graphically represents that IA$^{g7}$-B:12-22RE-Reg3 complex stimulates both BDC12-4.1 and BDC12-4.4 cells but not BDC2.5 cells.

As shown in FIG. 3, plate bound I-A$^{g7}$-B:12-22RE-Reg3 complex stimulated both BDC12-4.1 and BDC12-4.4 hybridoma cells, but did not stimulate the BDC2.5 hybridoma cells. Similarly, I-A$^{g7}$-B:12-23 complex stimulated both BDC12-4.1 and BDC12-4.4 hybridoma cells (data not shown.)

Example 3

This example illustrates that wild type NOD mice and DKO mice (NOD mice with both wild-type insulin genes knocked out) develop high titer antibodies to the I-A$^{g7}$-insulin autoantigenic peptide complex after immunization with the complex.

Animals:

NOD mice in which both native insulin sequences have been knocked out (Double Knock Out or DKO), but that contain a mutated proinsulin transgene (insulin B:Y16A substitution) were used for immunization (4). These mice were chosen because they recognize the native insulin Peptide B:9-23 as foreign and develop higher titers of antibodies against the I-A$^{g7}$-B:9-23 complex. In addition, these mice do not spontaneously develop insulin autoantibodies (IAA's). Young (3-4 weeks old) wild type NOD mice were also immunized to test if antibodies that block presentation of B:9-23 to T cell receptors can be generated in the non-mutated mice.

Target Molecules for Antibody Production:

The MHC class II molecule with covalently linked peptide provided a target for antibody generation. Generation of MHC class II with covalently linked peptide has been previously described (21). In the instant case, two insulin antigenic peptides, Insulin B:12-22RE(Reg3) having the amino acid sequence VERLYLVAGEE (SEQ ID NO:8) and insulin B:12-23 having the amino acid sequence VEALYLVCGERG (SEQ ID NO:2) were covalently linked to the I-A$^{g7}$ beta chain with a flexible linker sequence (QAGGGSLVPRGSGGGGS (SEQ ID NO:11) and GGGSLVPRGSGGGGS (SEQ ID NO:12), respectively). Baculoviral vectors containing constructs encoding the complexes I-A$^{g7}$-linker-insulin B:12-22RE(Reg3) and I-A$^{g7}$-linker-insulin B12-23 and control complex I-A$^{g7}$-linker-HEL11-23 were prepared. Hi5 cells were infected with the baculovirus to express each complex. The complexes were purified using affinity columns.

Wild type NOD mice and insulin B:Y16A DKO NOD mice were immunized with purified target I-A$^{g7}$-insulin B:12-22RE(Reg3) or I-A$^{g7}$-insulin B12-23 complex with or without Complete Freund's Adjuvant (CFA). Sera were harvested and processed at 2 and 4 weeks post immunization.

Figure 4:
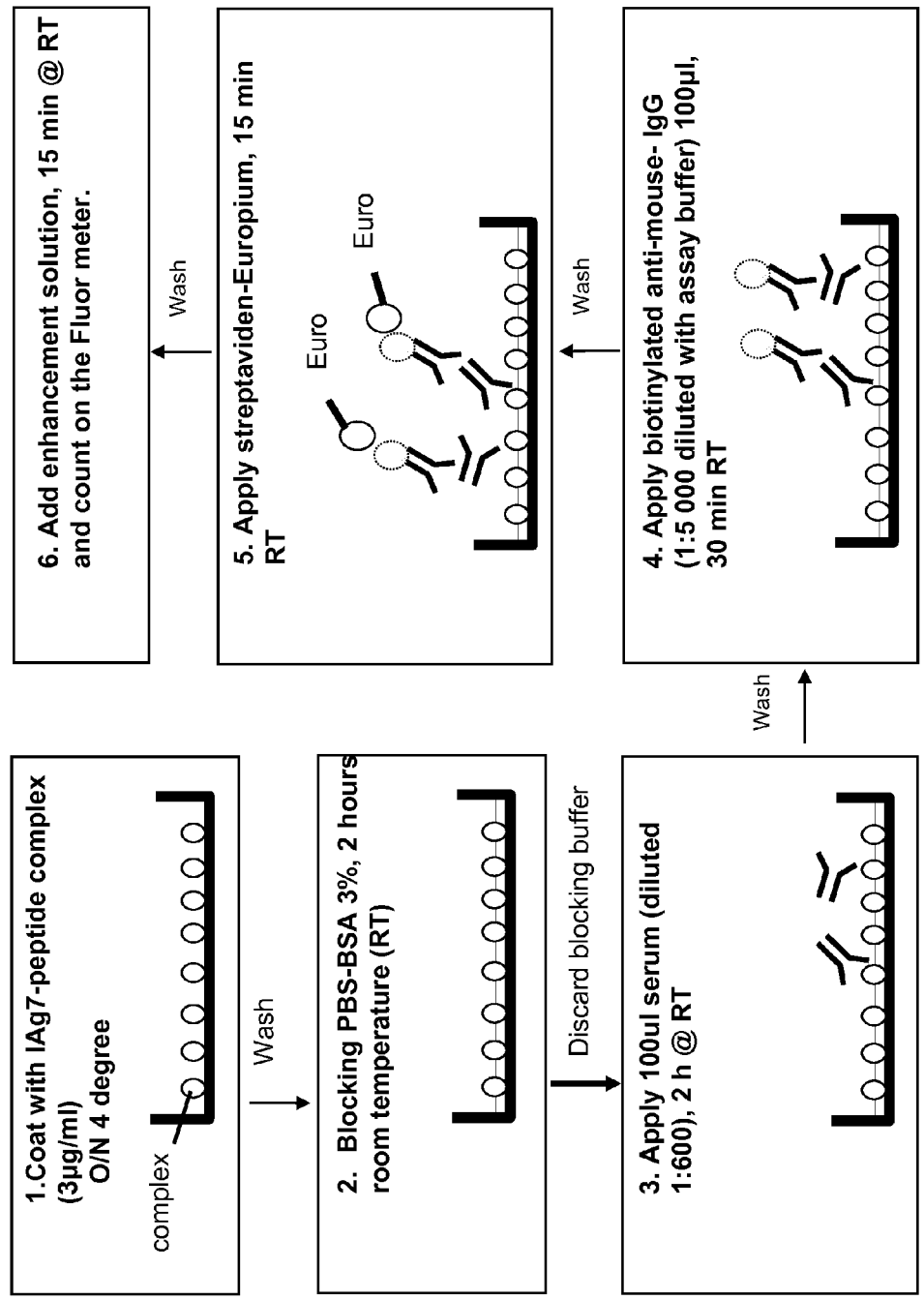
FIG. 4 is a schematic representation of the immunofluorometric anti-IA$^{g7}$ antibody assay.

At 2 weeks post immunization, multiple clonal antibodies reactive to I-A$^{g7}$-B insulin peptide developed. The specific antibodies which recognize I-A$^{g7}$-B insulin peptide but not I-A$^{g7}$-HEL11-23 are assumed to be the specific antibodies that would block T cell recognition. Presence of antibodies in the sera that are specific for a given I-A$^{g7}$-autoantigenic peptide complex was confirmed by performing solid-phase Europium based ELISA-type assay utilizing a sensitive Streptavidin-Europium detection system with time-resolved fluorescence. The Europium based ELISA assay for anti-I-A$^{g7}$ antibodies was set up based on the specific antigen-antibody reaction. FIG. 4 shows the schematic of the immunofluorometric anti-I-A$^{g7}$-peptide antibody assay. 96 well plates were coated with the complex that was used in immunization (e.g. I-A$^{g7}$-B:12-22RE-Reg3), blocked with 2% bovine serum album to reduce nonspecific binding and washed. After washing, diluted serum was added into the plate to allow binding between the anti-I-A$^{g7}$ antibody in the serum and the plate bound I-A$^{g7}$-peptide complex. Next, anti-mouse-IgG1-biotin was added to allow binding with the antibodies from serum. Next, Europium labeled streptavidin (DELFIA: 1244-360 from PerkinElmer Life and Analytical Sciences, Boston, Mass. diluted 1:2000 in assay buffer) was added. After washing with 300 µl washing buffer for 3 times, 200 µl of enhancement solution (DELFIA: 1244-105 from PerkinElmer Life and Analytical Sciences, Boston, Mass.) was added to plates and incubated for 25 min to achieve complete reaction. Finally, fluorescence was detected with a Wallac fluorimeter (Victor V 1420 Multilabel counter, Turku, Finland).

Figure 5:
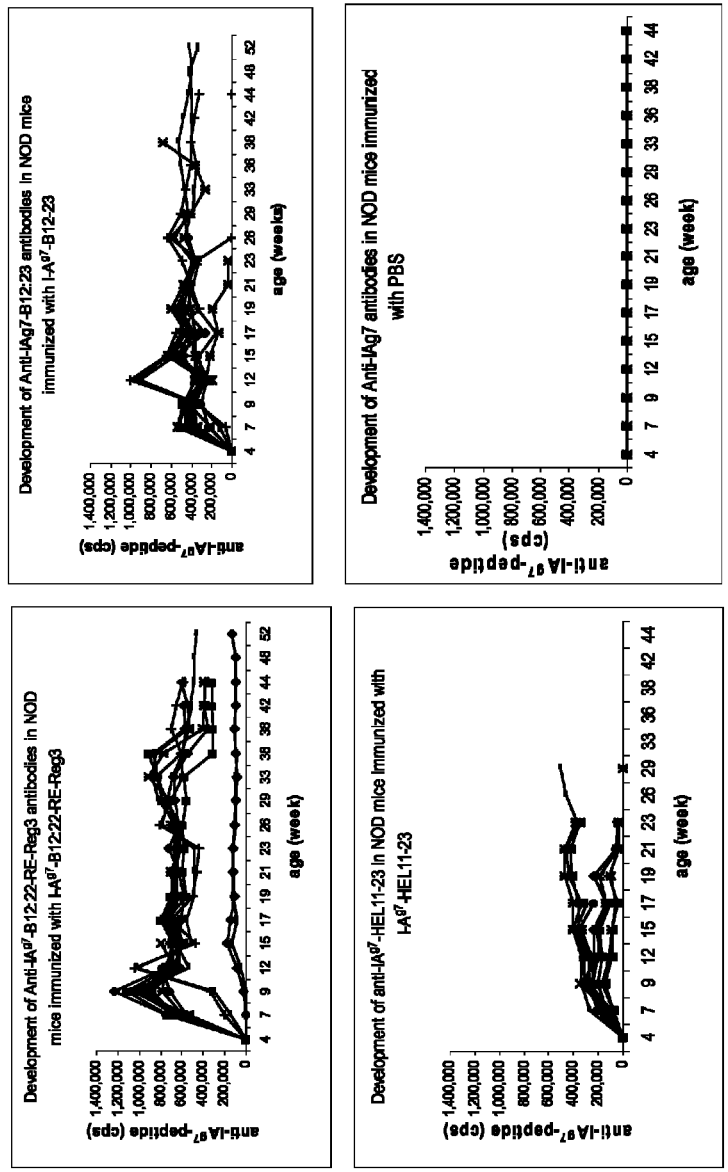
FIG. 5 shows that NOD mice develop high titer antibodies after immunization with IA$^{g7}$-B:12-22RE-Reg3 or IA$^{g7}$-B1:2-23 complex, but much lower titer antibodies in IA$^{g7}$-HEL11-23 treated mice. 2 weeks post immunization most mice developed antibodies and at 4 weeks post-immunization higher titer antibodies were observed. Stronger titers were observed post-boost immunization at 11 weeks old or 7 weeks post-immunization.

As shown in FIG. 5 immunized mice developed antibodies to the I-A$^{g7}$-peptide complexes. FIG. 5 shows results obtained from NOD mice that were immunized and were followed for up to 52 weeks of age. Four week old mice were immunized with I-A$^{g7}$-B:12-22RE(Reg3), IA$^{g7}$-B:12-23, IA$^{g7}$-HEL11-23, or PBS. Two weeks after immunization, anti-IA$^{g7}$-peptide complex antibodies were detected in the sera. Antibody reactivity persisted and increased at 4 weeks post immunization in most mice. All the mice were boosted with 100 µg complex at 11 weeks of age. Higher titer antibodies developed and persisted (but not in the PBS immunized group). I-A$^{g7}$-B:12-22RE(Reg3) appeared to be the most pathogenic.

Figure 7:
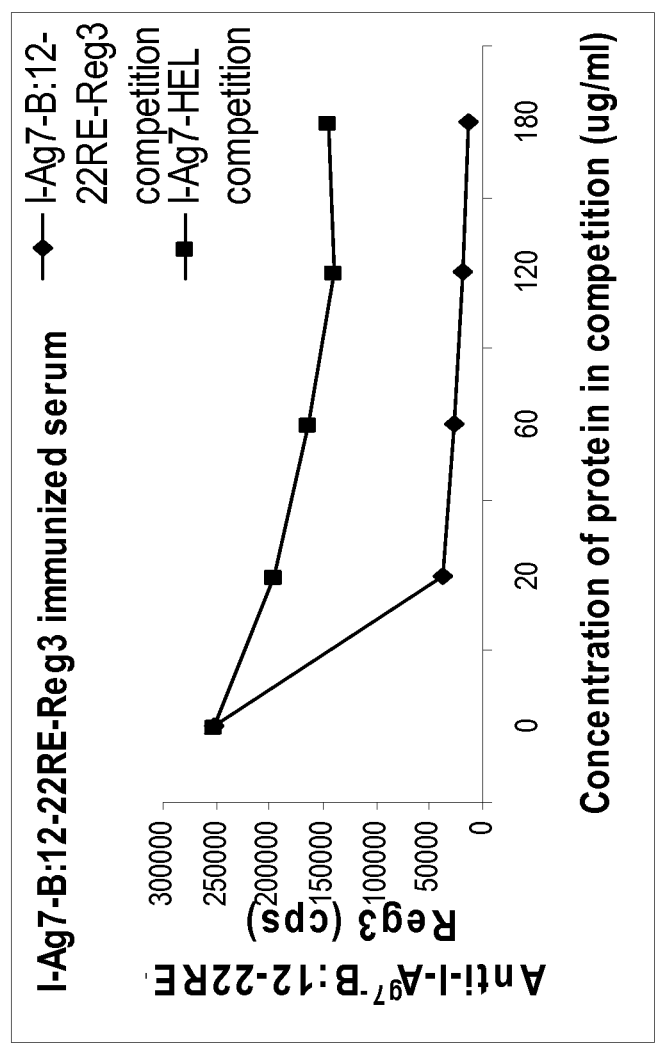
FIG. 7 shows that IA$^{g7}$-B:12-22RE-Reg3 complex absorbed the antibodies completely but the IA$^{g7}$-HEL11-23 complex did not which suggests that antibodies specific against the IA$^{g7}$-B:12-22RE-Reg3 epitope recognized by T cells exist in the serum.

To test specificity of the general antibodies, the antibodies were analyzed with I-A$^{g7}$-peptide complex in a fluid phase incubation prior to addition of antibodies to wells in the assay described above. Either the I-A$^{g7}$-B:12-23 complex or I-A$^{g7}$-B:12-22RE(Reg3) complex or I-A$^{g7}$-HEL11-23 were coated onto the plates; the sera were competed with I-A$^{g7}$-B:12-23 complex or I-A$^{g7}$-B:12-22RE-Reg3 complex or I-A$^{g7}$-HEL11-23 for one hour at room temperature before performing the antibody binding assay as described before. FIGS. 6 and 7 respectively show that the antibodies were effectively absorbed with I-A$^{g7}$-B:12-23 complex or I-A$^{g7}$-B:12-22RE(Reg3) complex but not with I-A$^{g7}$-HEL11-23 complex, indicating the presence of the specific antibodies against I-A$^{g7}$-B:12-23 or against I-A$^{g7}$-B:12-22RE(Reg3) in the serum. The data shown in the figures is with serum taken from the I-A$^{g7}$-B:12-22RE(Reg3) immunized mice, diluted 1:4800 and with serum from I-A$^{g7}$-B:12-23 immunized mice, diluted 1:3600 from 10 weeks old mice.

Example 4

This Example illustrates that the generated antibodies are able to specifically inhibit stimulation of the BDC12-4.1 T cell hybridoma cells by the B:9-23 peptide loaded antigen presenting cells (APC).

Figure 8:
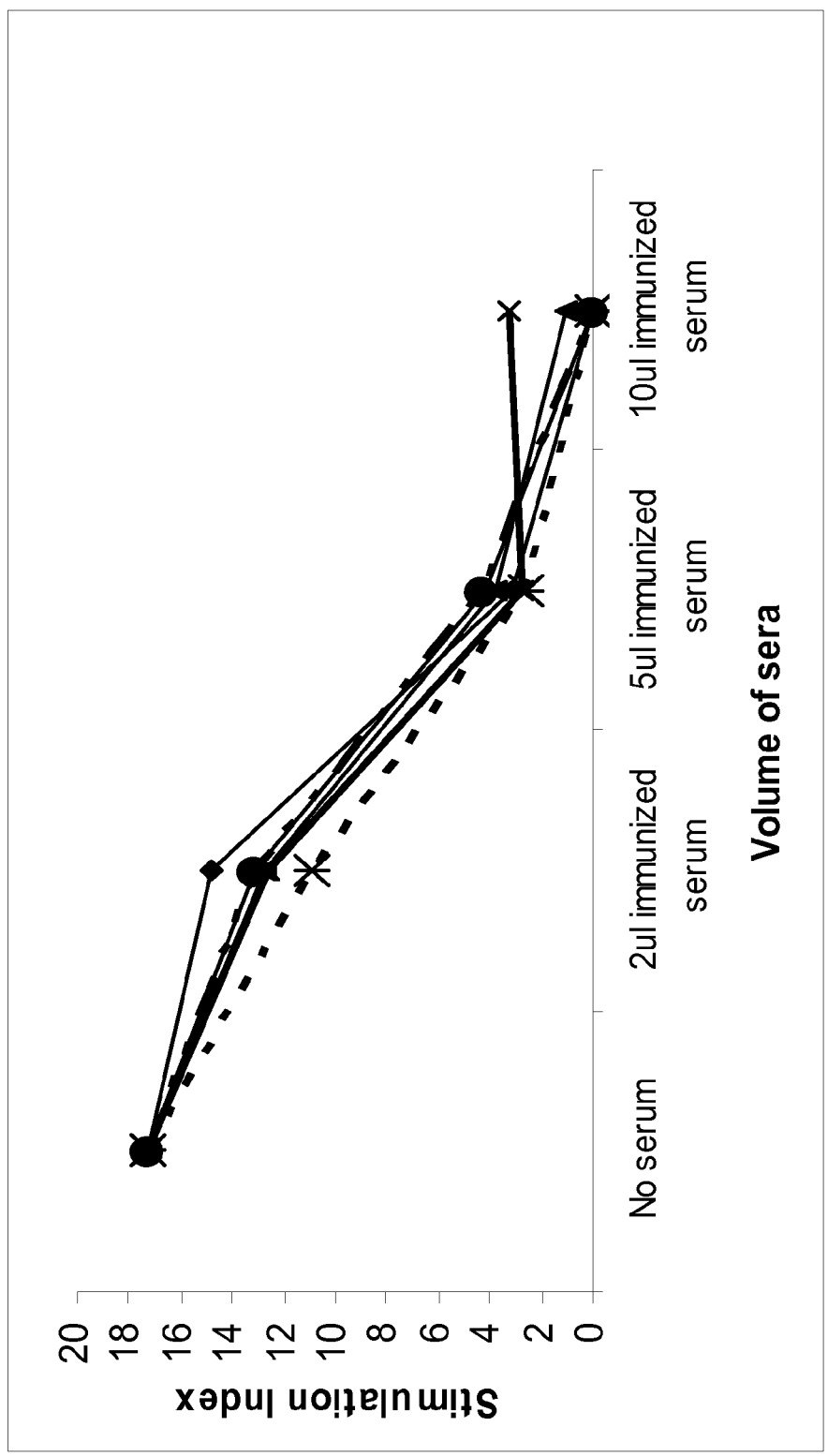
FIG. 8 shows that the sera obtained from different mice immunized with IA$^{g7}$-B:12-22RE-Reg3 complex or IA$^{g7}$-B:12-23 inhibited The BDC12-4.1 T cell response to the insulin2:B9-23 peptide in a dose dependent manner.

FIG. 8 shows that the serum obtained from the mice inhibited the BDC12-4.1 T cell response to the insulin B:9-23 peptide in a dose dependent manner. Mice were immunized with I-A$^{g7}$-B:12-23 complex or I-A$^{g7}$-HEL11-23 complex. NOD spleen cells (1×10$^5$ cells/100 µl/well) were used as antigen presenting cells. Insulin2 B:9-23 peptide was used as stimulating peptide. NOD splenocytes were incubated in PBS with insulin B:9-23 peptide for 2 hours at 37° C. to permit the APCs to bind to the peptide. 20,000 BDC12-4.1 T-cell hybridoma cells and varying volumes of serum were added. Sera from pre-immunization NOD mice were used as control. As shown in FIG. 8, B:9-23 peptide induced 100% response to hybridomas, the stimulation index (SI) was calculated by comparing the response to peptide to background without stimulation.

Figure 9:
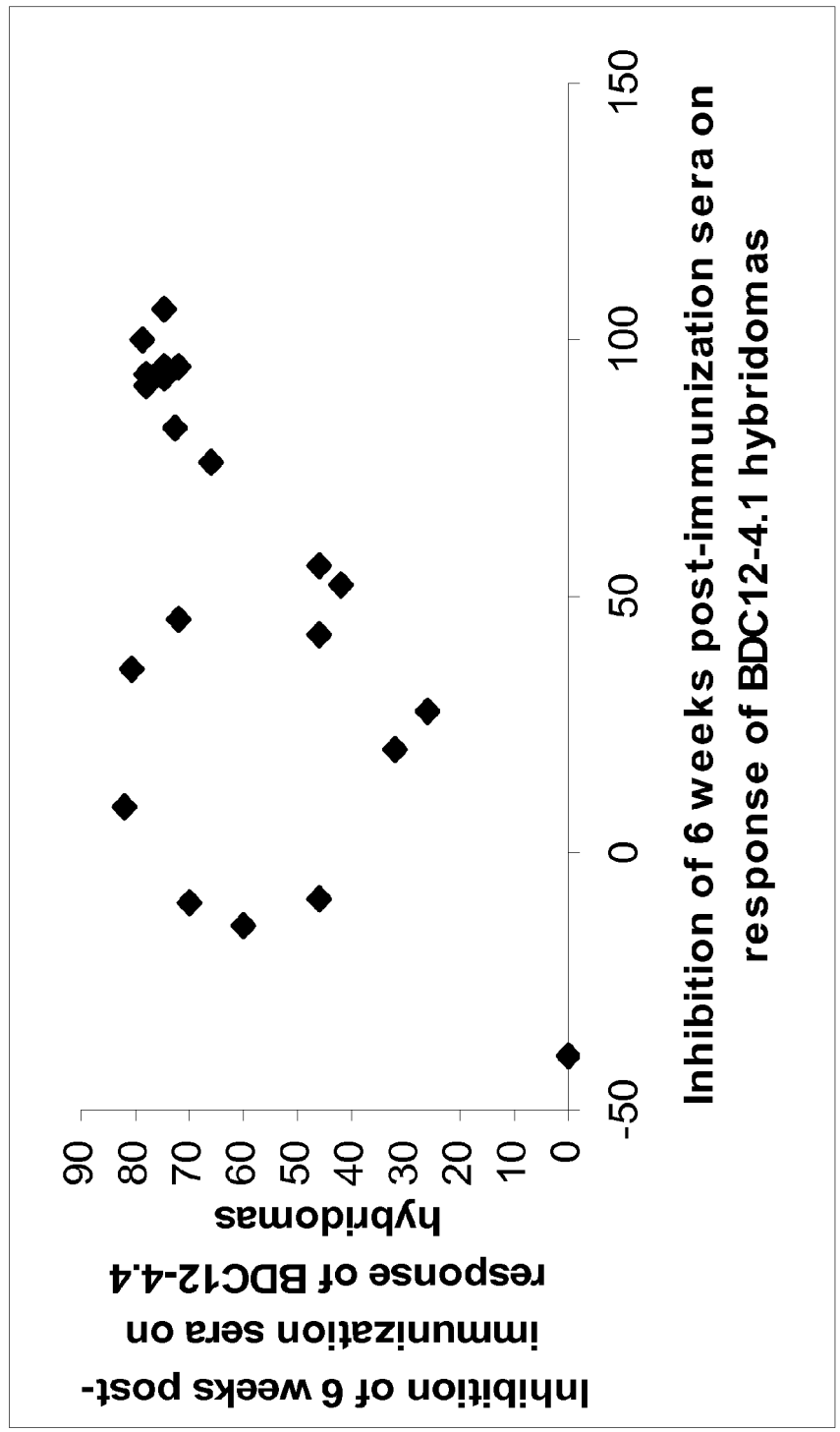
FIG. 9 shows that the sera from mice immunized with I-A$^{g7}$-B:12-22RE-Reg3 complex or I-A$^{g7}$-B:12-23 complex inhibit the responses of both BDC12-4.1 and BDC12-4.4 cells.
Figure 10:
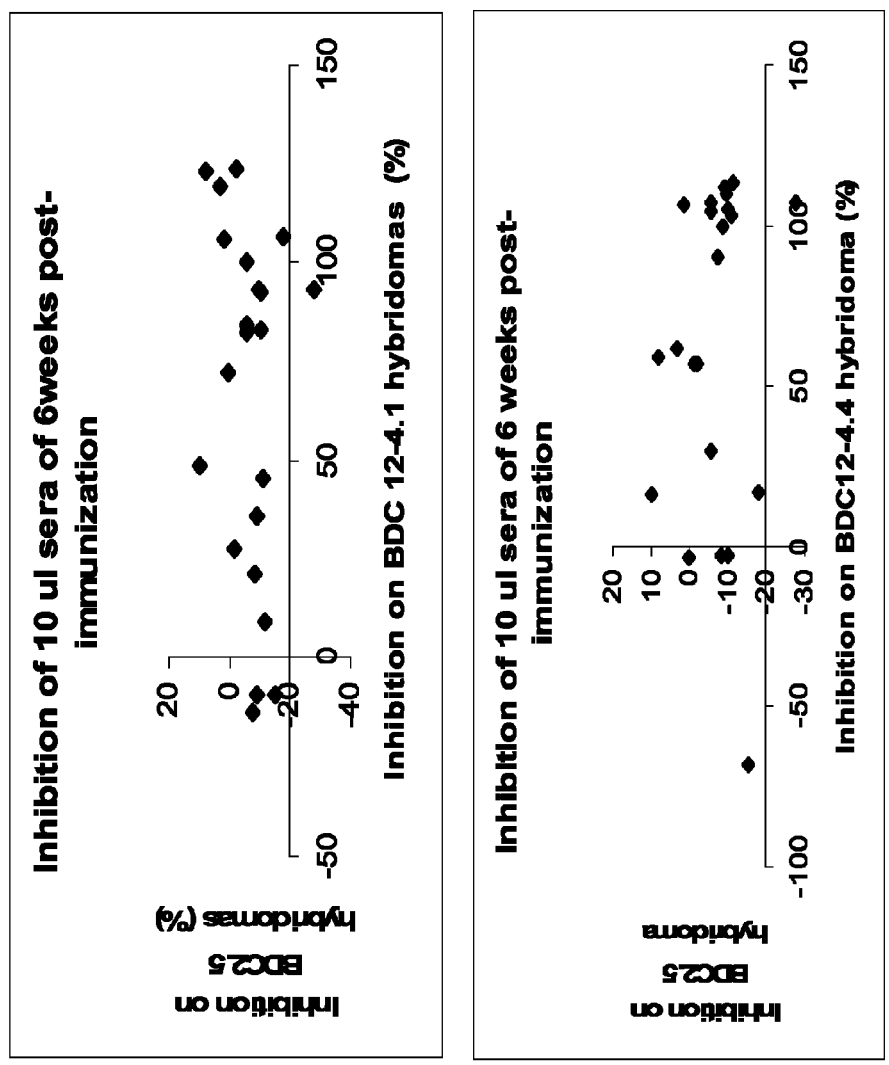
FIG. 10 shows that the inhibition effect of the sera from mice immunized with I-A$^{g7}$-B:12-22RE-Reg3 complex or I-A$^{g7}$-B:12-23 complex is specific, as the sera inhibit the responses of both BDC12-4.1 and BDC12-4.4 cells, but not that of BDC2.5 cells stimulated with the mimotope.

The BDC2.5 hybridoma was used as control cells to illustrate the specificity of the inhibition effect. Both BDC12-4.1 and BDC12-4.4 hybridomas recognize insulin B:9-23 peptide (including different registers). BDC2.5 cells, which were also isolated from pancreatic lymph node cells of non-diabetic NOD (same as BDC12-4.1 and BDC12-4.4 cells), recognize a peptide mimotope (HRPI-RM), instead of B:9-23 peptide. FIG. 9 shows that antibodies obtained from mice immunized with I-A$^{g7}$-B12:22 RE-Reg3 complex or I-A$^{g7}$-B12:23 complex inhibited the responses of both BDC12-4.1 and BDC12-4.4 cells, both of which express the TRAV5D-4*04 containing TCR and recognize the B:9-23 peptide. However, as can be seen in FIG. 10, the sera did not inhibit the response of BDC 2.5 hybridoma cells to its mimotope peptide.

Example 5

This Example illustrates that the antibodies from Example 2 are able to specifically inhibit peak insulin autoantibodies (IAA), a predictor of diabetes in mice.

Figure 11:
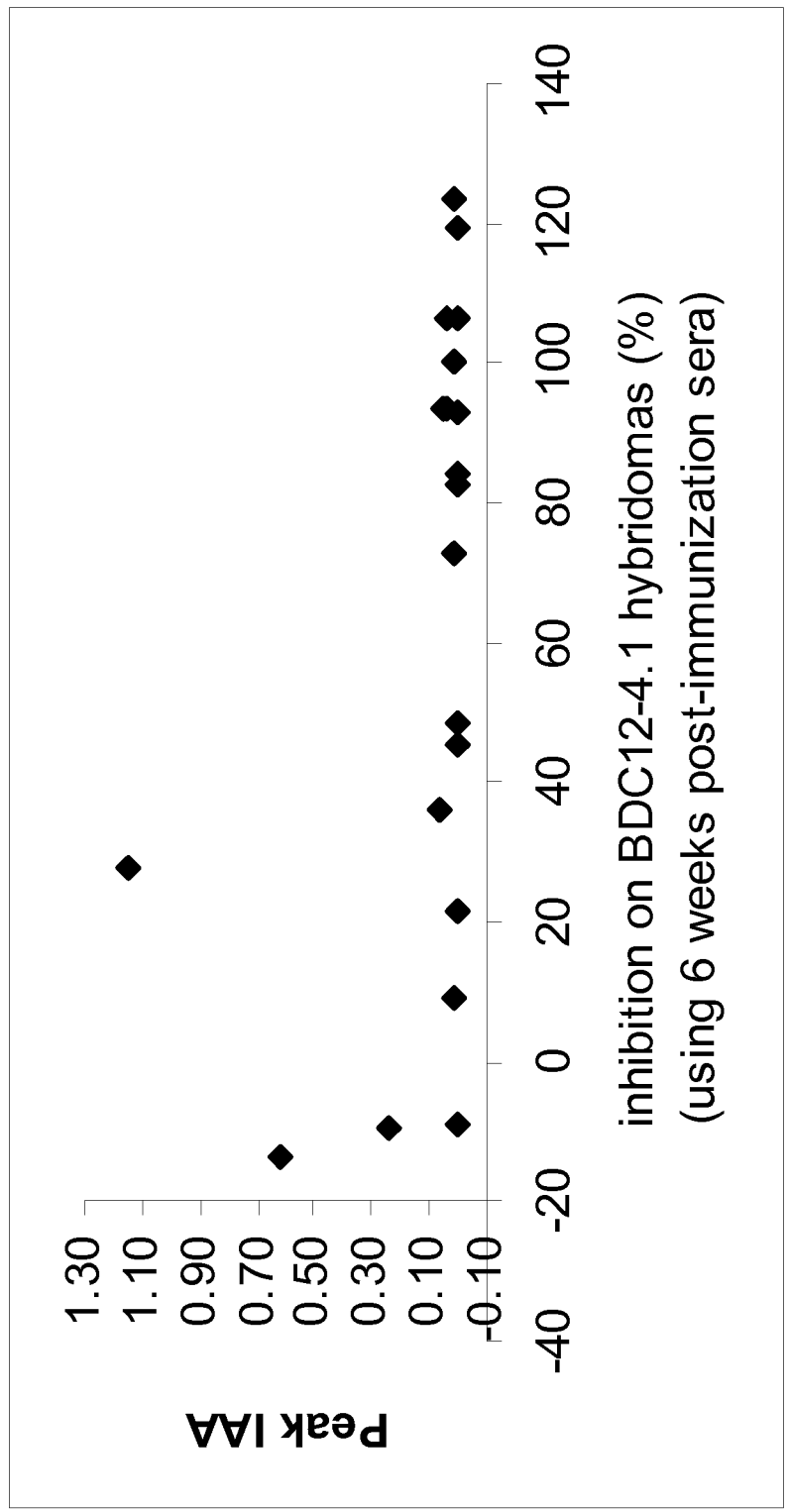
FIG. 11 shows the inhibition effect of the sera on BDC12-4.1 cells vs. peak insulin autoantibodies (IAA) in immunized mice. The sera which showed stronger inhibition effect had a low or negative IAA value.

FIG. 11 is a graphical representation of the inhibition effect on BDC12-4.1 cells versus peak insulin autoantibodies (IAA) in mice immunized with the anti I-A$^{g7}$-B12:23 complex. As shown in the figure, the sera which showed stronger inhibition effects (sera having higher than 40% inhibition effect) are associated with a low or negative IAA value. The three sera which have high IAA exhibit low inhibition (27%) or no inhibition at all. Thus, presence of high titer antibodies correlates with low IAA, an index used for predicting diabetes, suggesting that the anti-complex antibodies would be effective in treating or preventing diabetes.

Example 6

This example illustrates that immunization of mice with the I-A$^{g7}$-B12:23 or the I-A$^{g7}$-B12:22 RE-Reg3 suppresses diabetes in wild type NOD mice.

Figure 12:
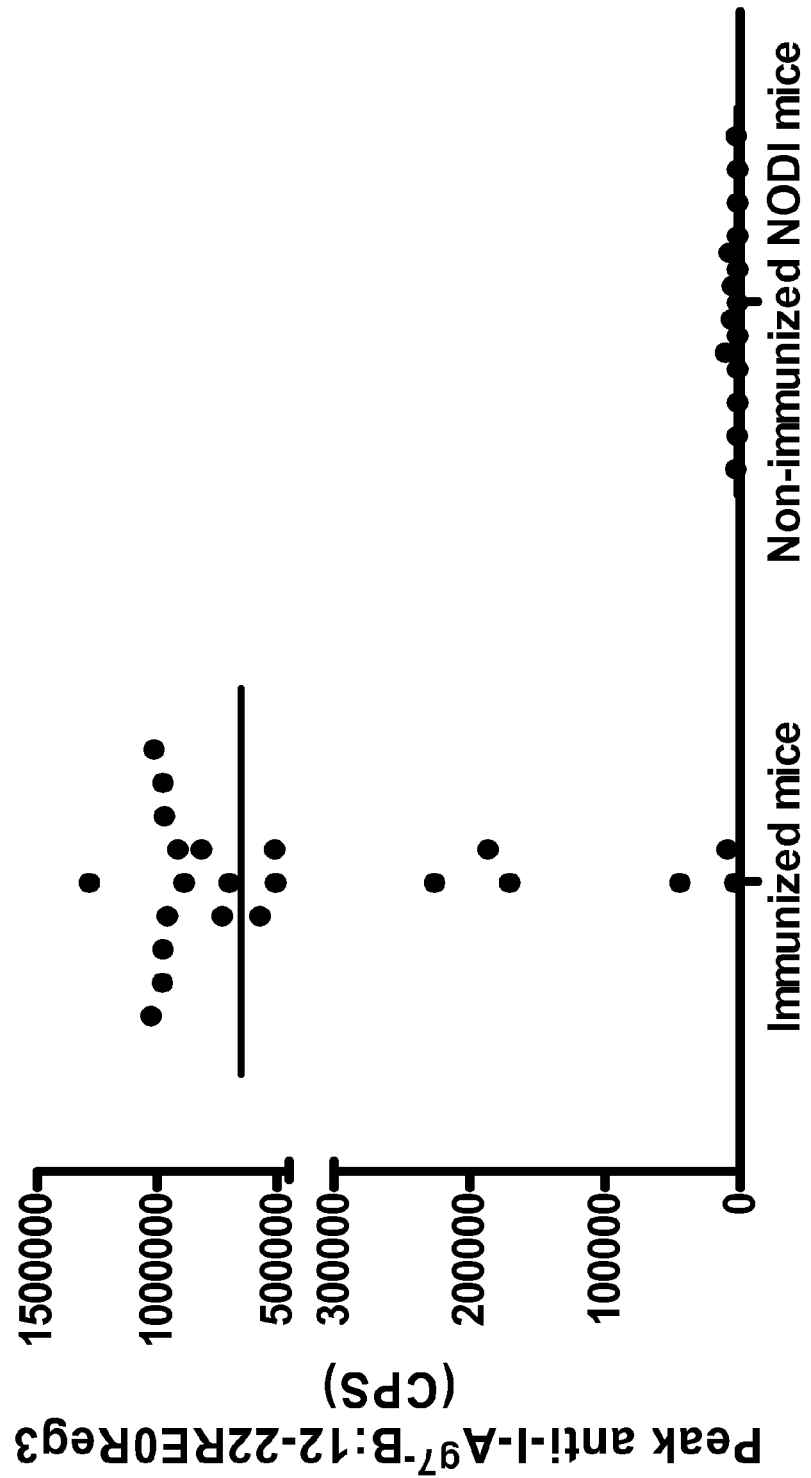
FIG. 12 shows the production of anti-IA$^{g7}$-B:12-22RE-Reg3 antibodies in immunized and non-immunized mice, indicating that most mice developed antibodies successfully post-immunization.

FIG. 12 illustrates the anti-I-A$^{g7}$ titer difference between immunized mice and non-immunized mice. Non-immunized mice were all NOD mice. Most immunized mice developed high titer antibodies after immunization, but two out of 22 immunized mice did not develop antibodies. 1200 CPS (approximately the mean+3SD of normal control's anti-I-A$^{g7}$) was used as cut-off to divide immunized mice as anti-I-A$^{g7}$ antibody positive group and negative group. Blood glucose was monitored and diabetes was diagnosed with repeated blood glucose higher than 250 mg/ml. Consistent with the lack of development of antibodies, the two antibody-negative mice developed diabetes at around 18 weeks old. None of the mice that received immunization with I-A$^{g7}$-peptide and expressed antibodies developed diabetes.

Figure 13:
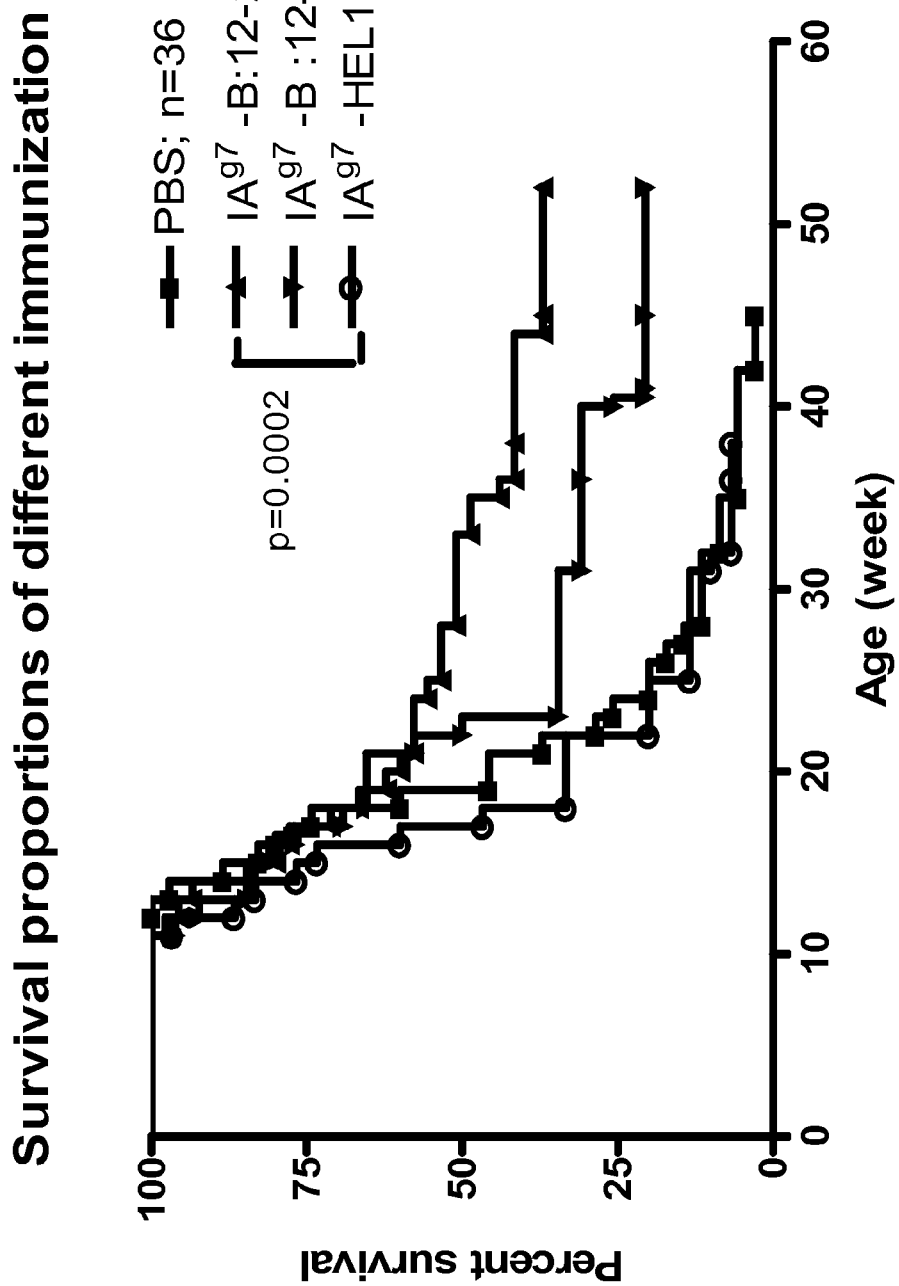
FIG. 13 shows life tables of NOD mice that were immunized with either IA$^{g7}$-B:12-22RE-Reg3, IA$^{g7}$-B:12-23, IA$^{g7}$-HEL11-23, or PBS and shows that the development of diabetes was significantly delayed in mice that were immunized with the I-A$^{g7}$-B:12-22RE-Reg3 complex.

FIG. 13 shows about 50% long term prevention of diabetes in I-A$^{g7}$-B:12-22RE-Reg 3 complex immunized mice (P=0.0005 vs. PBS treated mice; P=0.0002 vs. I-A$^{g7}$-HEL11-23 treated mice). Around 50% of the immunized mice maintained normal blood glucose levels even at 52 weeks of age but almost all I-A$^{g7}$-HEL11-23 complex immunized and PBS treated mice developed diabetes much earlier. I-A$^{g7}$-B:12-23 complex immunized mice showed the same trend but not significantly delayed diabetes (P=0.0518 vs. PBS treated mice).

Figure 14:
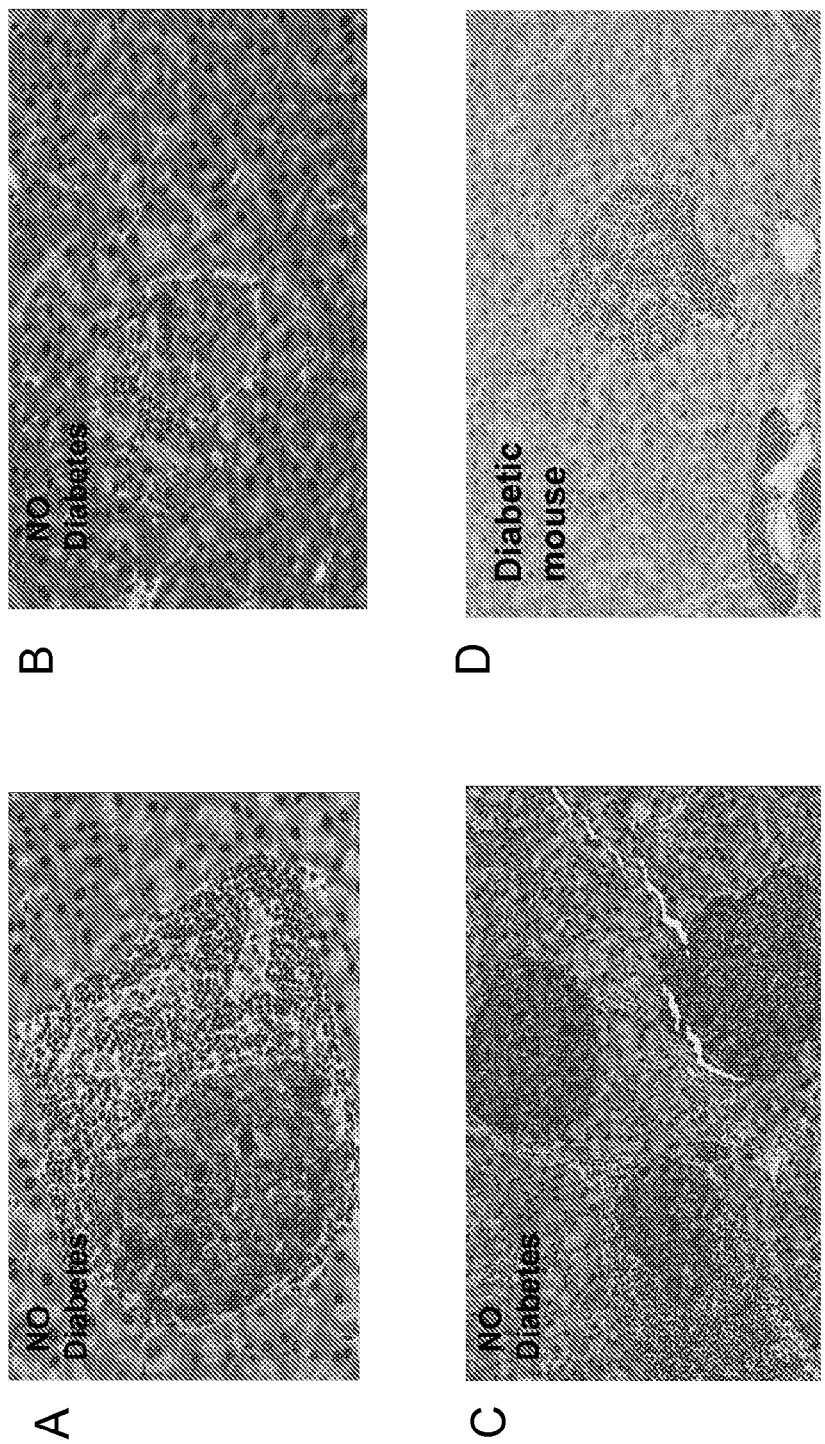
FIG. 14 shows that immunized mice in which diabetes was prevented show insulin islet retention at 52 weeks. Panels A, B and C show insulin staining from three different mice that were immunized with I-A$^{g7}$-B:12-22RE-Reg3. These mice have peri-insulitis but show insulin islet retention. Panel D shows insulin staining from a diabetic mouse and shows no insulin retention in islet.

Further, all the mice in which diabetes was prevented were sacrificed at 52 weeks of age and the pancreas were stained for insulin to evaluate insulin retention. The results are shown in FIG. 14. FIG. 14A, B and C shows islets from three different mice that were immunized with I-A$^{g7}$-B:12-22RE-Reg3 and that did not develop diabetes; these mice show significant islet insulin retention. In contrast, FIG. 14D shows islets from a diabetic control mouse (immunized with PBS) at 30 weeks old; the mouse shows complete insulitis and does not show insulin islet retention.

Example 7

This example illustrates the generation of anti-I-A$^{g7}$-B12:22 RE-Reg3 monoclonal antibodies.

Figure 15A:
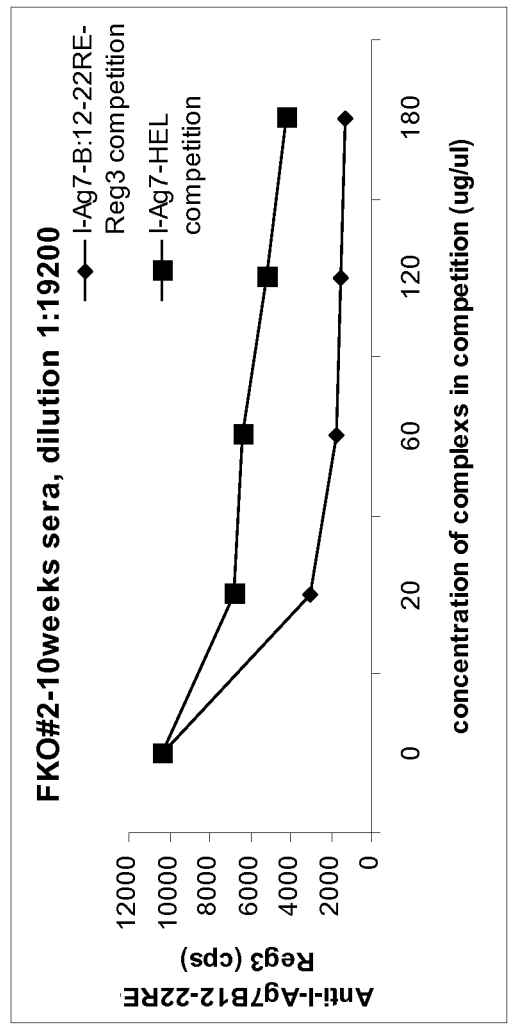
FIG. 15A shows the generation of monoclonal antibodies in NOD mice.
Figure 15A:
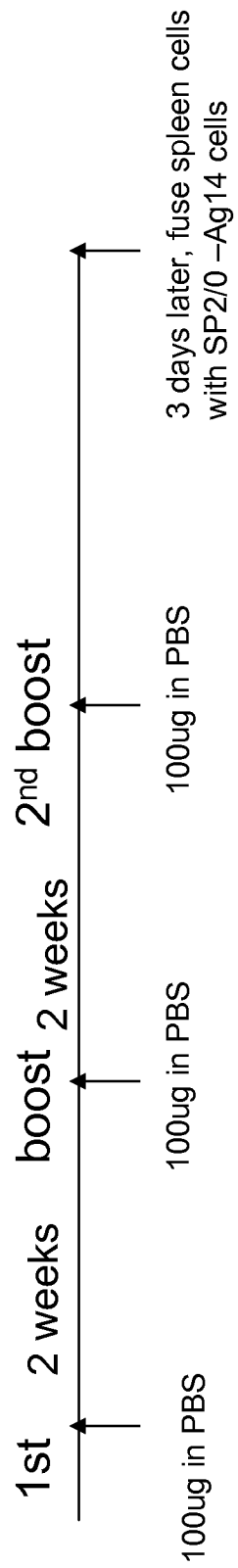

FKO#2 mouse was immunized with IA$^{g7}$-B:12-22RE-Reg3 complex and boosted twice with two weeks interval. As can be seen in FIG. 15A, the serum was absorbed by I-A$^{g7}$-B:12-22RE-Reg3 but not by I-A$^{g7}$-HEL11-23, which indicating the presence of the I-A$^{g7}$-B:12-22RE-Reg3 specific antibodies in the sera. Three days later after the last immunization, the spleen was removed and the spleen cells were fused with SP2/0—Ag14 cells to create various hybridoma clones.

Figure 15B:
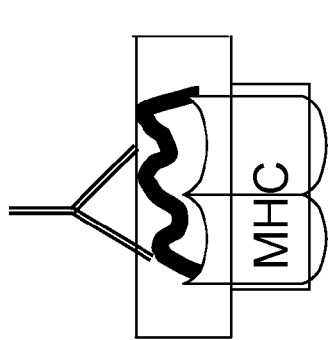
FIG. 15B shows that six hybridomas produced monoclonal anti IA$^{g7}$-B:12-22RE-Reg3 antibodies.
Figure 15B:
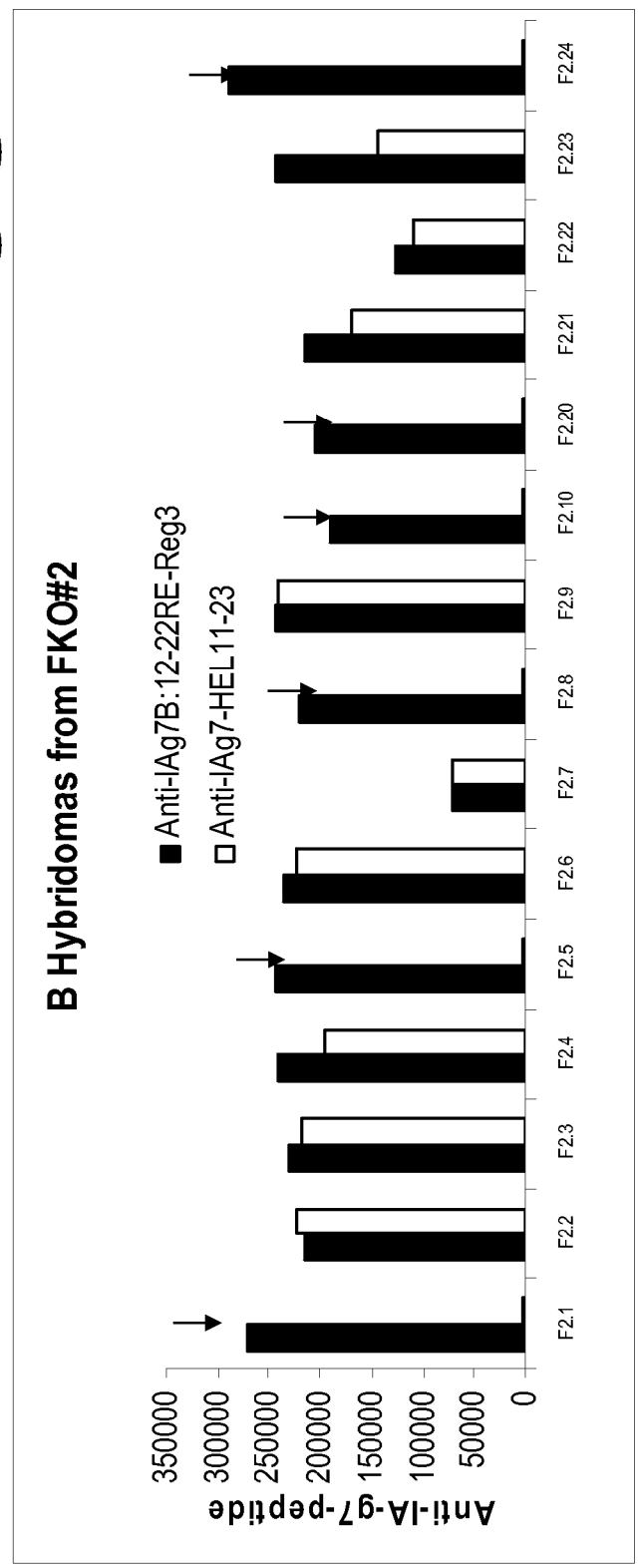
Figure 15C:
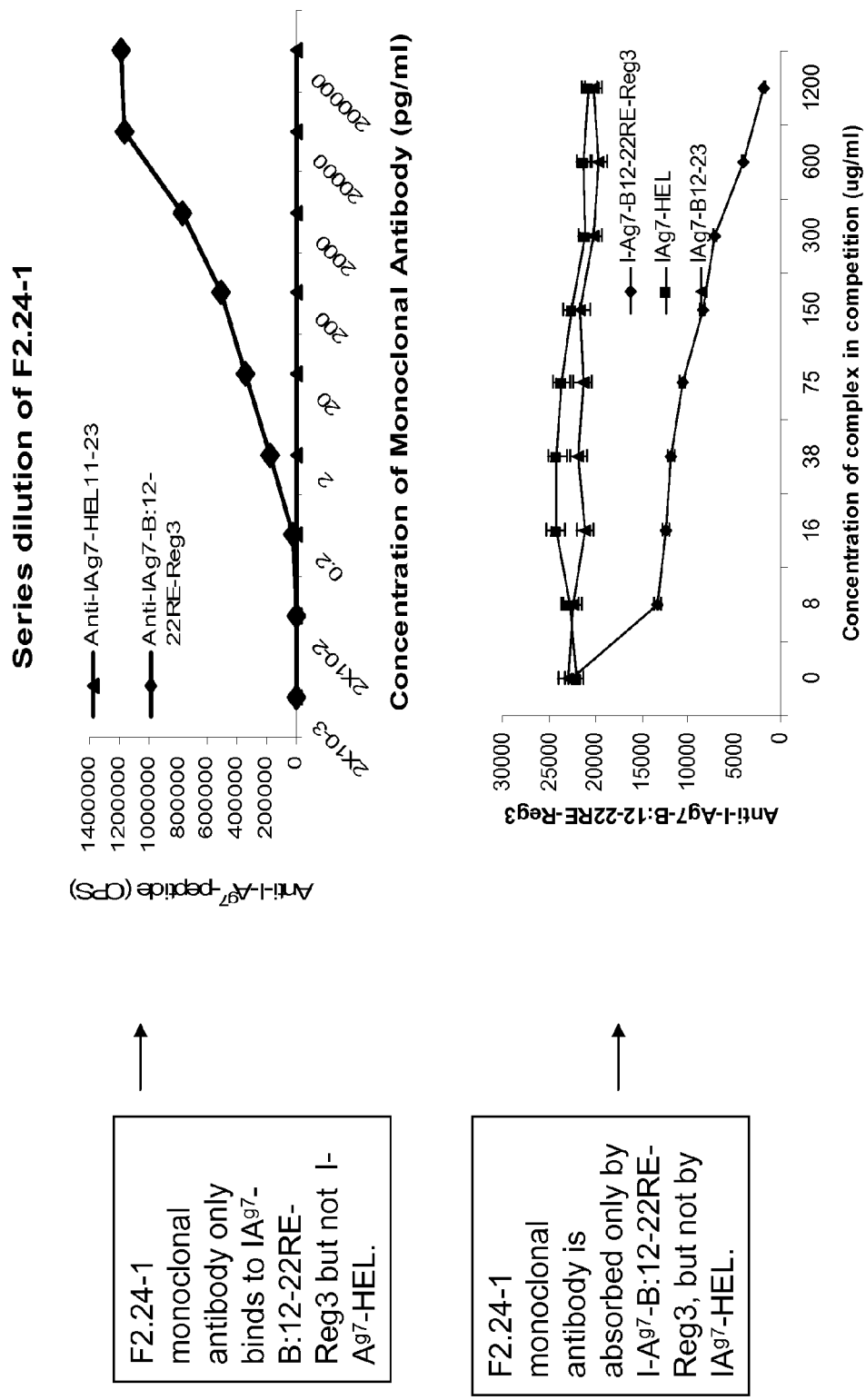
FIG. 15C shows that the F2.24-1 anti-IA$^{g7}$-B:12-22RE-Reg3 monoclonal antibody specifically binds to IA$^{g7}$-B:12-22-Reg3.

400 hybridoma clones were tested. Out of these only 6 produced antibodies that bound to only IA$^{g7}$-B:12-22RE-Reg3, but not to IA$^{g7}$-HEL11-23. See FIG. 15B. The remaining 394 hybridomas produced antibodies that recognize epitope not specific for register 3, but epitopes common in I-A$^{g7}$-B:12-22RE-Reg3 and I-A$^{g7}$-HEL11-23 such as epitope on I-A$^{g7}$. After sub-cloning of the IA$^{g7}$-B:12-22RE-Reg3 binding cell lines, the monoclonal antibody to IA$^{g7}$-B: 12-22RE-Reg3, named F2.24-1, was identified. The specificity of F2.24-1 was tested with competition assay. F2.24-1 was diluted to 1 pg/ml (which gave anti-I-A$^{g7}$-B:12-22RE-Reg3 signal of 22000 cps) for the absorption assay. As expected, F2.24-1 was not absorbed by I-A$^{g7}$-HEL11-23 and I-A$^{g7}$-B: 12-23 (see FIG. 15C). The monoclonal antibody F2.24-1 was used in the subsequent experiments.

Example 8

This example illustrates that the monoclonal antibody F2.24-1 inhibits B:9-23 responsive T cells.

Figure 16:
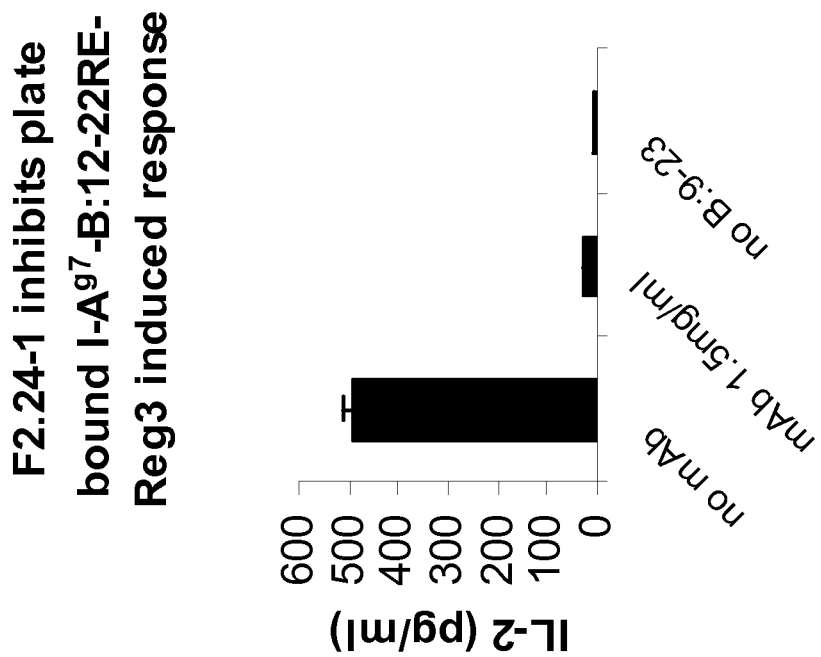
FIG. 16 shows that the F2.24-1 monoclonal antibody inhibits B:9-23 responsive T cells.
Figure 16:
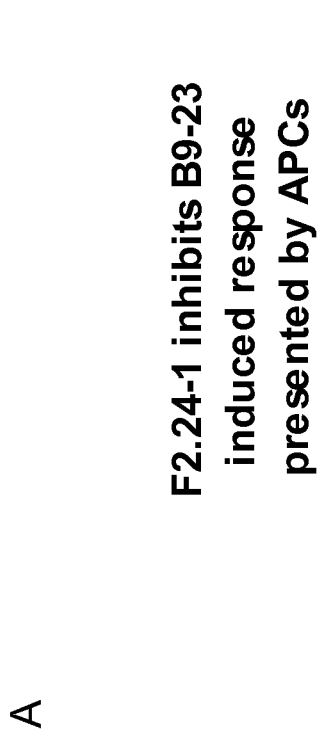
Figure 17:
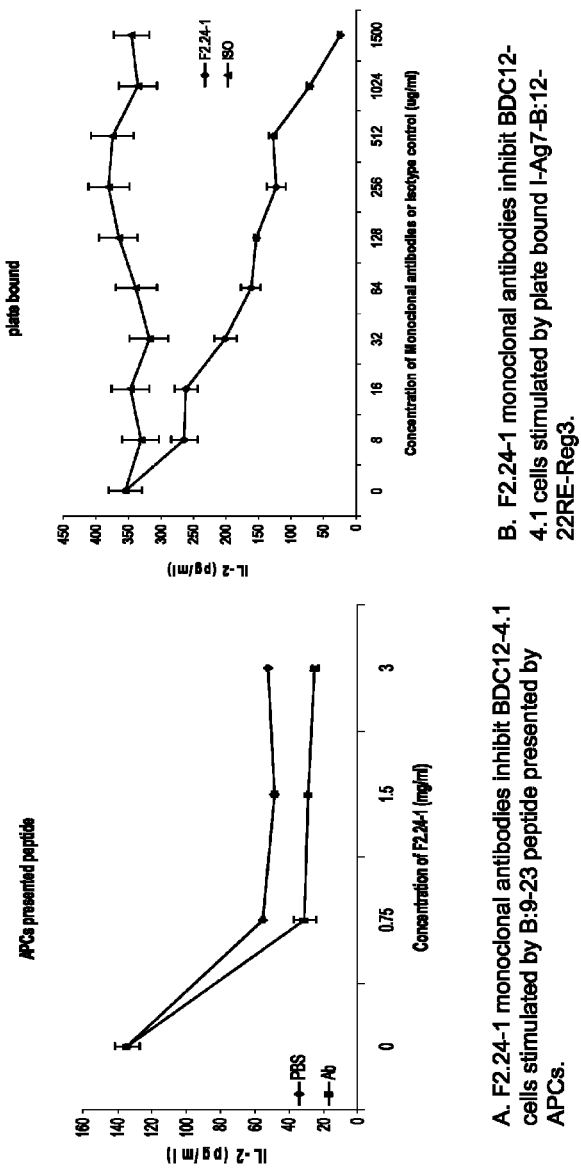
FIG. 17 shows that the F2.24-1 monoclonal antibody inhibits B:9-23 responsive T cells.

The B:9-23 peptide induced response of BDC12-4.1 hybridomas with or without F2.24-1 monoclonal antibodies was compared. As shown in FIG. 16A, the F2.24-1 monoclonal antibodies inhibited response to B:9-23 presented by APCs. Similarly, F2.24-1 inhibited response to plate bound IA$^{g7}$-B: 12-22RE-Reg3. (See FIG. 16B). FIG. 17 shows that F2.24-1 inhibits BDC12-4.1 hybridomas in a dose dependent manner.

Example 9

This example illustrates that the monoclonal antibody F2.24-1 inhibits development of insulin autoantibodies.

Figure 18:
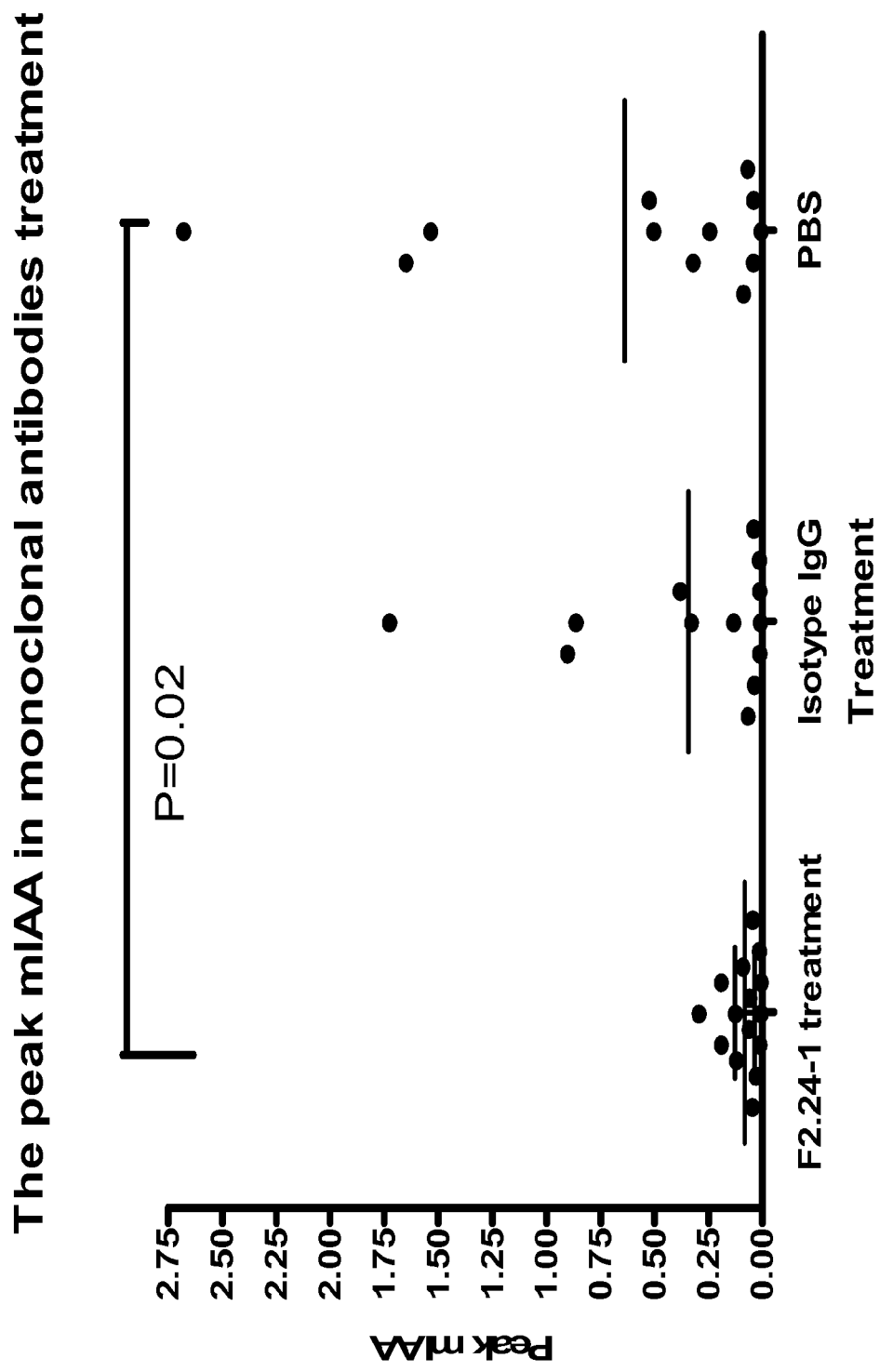
FIG. 18 shows that the F2.24-1 monoclonal antibody inhibits development of insulin autoantibodies.

Insulin autoantibodies are used as a predictor of insulitis and diabetes. Insulin autoantibodies were monitored every two weeks and the maximum value was analyzed in each mouse. As shown in the FIG. 18, the mice treated with F2.24-1 monoclonal antibodies all have lower insulin autoantibodies value than isotype IgG treated mice and PBS treated mice, suggesting that the F2.24-1 monoclonal antibodies inhibit the onset of diabetes.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

REFERENCE LIST

1. Faideau, B., Briand, J. P., Lotton, C., Tardivel, I., Halbout, P., Jami, J., Elliott, J. F., Krief, P., Muller, S., Boitard, C. et al 2004. Expression of preproinsulin-2 gene shapes the immune response to preproinsulin in normal mice. *J Immunol.* 172:25-33.
2. Moriyama, H., Abiru, N., Paronen, J., Sikora, K., Liu, E., Miao, D., Devendra, D., Beilke, J., Gianani, R., Gill, R. G. et al 2003. Evidence for a primary islet autoantigen (preproinsulin 1) for insulitis and diabetes in the nonobese diabetic mouse. *Proc Natl Acad Sci USA.* 100:10376-10381.
3. Fife, B. T., Guleria, I., Bupp, M. G., Eagar, T. N., Tang, Q. Z., Bour-Jordan, H., Yagita, H., Azuma, M., Sayegh, M. H., and Bluestone, J. A. 2006. Insulin-induced remission in new-onset NOD mice is maintained by the PD-1-PD-L1 pathway. *Journal of Experimental Medicine* 203:2737-2747.
4. Nakayama, M., Abiru, N., Moriyama, H., Babaya, N., Liu, E., Miao, D., Yu, L., Wegmann, D. R., Hutton, J. C., Elliott, J. F. et al 2005. Prime role for an insulin epitope in the development of type 1 diabetes in NOD mice. *Nature* 435: 220-223.
5. Nakayama, M., Beilke, J. N., Jasinski, J. M., Kobayashi, M., Miao, D., Li, M., Coulombe, M. G., Liu, E., Elliott, J. F., Gill, R. G. et al 2007. Priming and effector dependence on insulin B:9-23 peptide in NOD islet autoimmunity. *J. Clin. Invest.* 117:1835-1843.
6. Wicker, L. S., Clark, J., Fraser, H. I., Garner, V. E., Gonzalez-Munoz, A., Healy, B., Howlett, S., Hunter, K., Rainbow, D., Rosa, R. L. et al 2005. Type 1 diabetes genes and pathways shared by humans and NOD mice. *J. Autoimmun.* 25 Suppl:29-33. Epub@2005 Oct. 28:29-33.
7. Wallis, R. H., Wang, K., Marandi, L., Hsieh, E., Ning, T., Chao, G. Y., Sarmiento, J., Paterson, A. D., and Poussier, P. 2009. TYPE 1 DIABETES IN THE BB RAT: A POLYGENIC DISEASE. *diab.*
8. Hattori, M., Buse, J. B., Jackson, R. A., Glimcher, L., Dorf, M. E., Minami, M., Makino, S., Moriwaki, K., Korff, M., Kuzuya, H. et al 1986. The NOD mouse: recessive diabetogenic gene within the major histocompatibility complex. *Science* 231:733-735.
9. Fujisawa, T., Ikegami, H., Noso, S., Yamaji, K., Nojima, K., Babaya, N., Itoi-Babaya, M., Hiromine, Y., Kobayashi, M., Makino, S. et al 2006. MHC-linked susceptibility to type 1 diabetes in the NOD mouse: further localization of Idd16 by subcongenic analysis. *Ann. N.Y. Acad. Sci.* 1079:118-21:118-121.
10. Todd, J. A., Acha-Orbea, H., Bell, J. I., Chao, N., Fronek, Z., Jacob, C. O., McDermott, M., Sinha, A. A., Timmerman, L., Steinman, L. et al 1988. A molecular basis for WIC class II associated autoimmunity. *Science* 240:1003-1009.
11. Corper, A. L., Stratmann, T., Apostolopoulos, V., Scott, C. A., Garcia, K. C., Kang, A. S., Wilson, I. A., and Teyton, L. 2000. A structural framework for deciphering the link between I-Ag7 and autoimmune diabetes. *Science* 288: 505-511.
12. Hovhannisyan, Z., Weiss, A., Martin, A., Wiesner, M., Tollefsen, S., Yoshida, K., Ciszewski, C., Curran, S. A., Murray, J. A., David, C. S. et al 2008. The role of HLA-DQ8 beta57 polymorphism in the anti-gluten T-cell response in coeliac disease. *Nature* 456:534-538.
13. Kanagawa, O., Shimizu, J., and Unanue, E. R. 1998. The role of I-A$^{g7}$□ chain in peptide binding and antigen recognition by T cells. *Int Immunol* 9:1523-1526.
14. Suri, A., and Unanue, E. R. 2005. The Murine Diabetogenic Class II Histocompatibility Molecule I-A(g7): Structural and Functional Properties and Specificity of Peptide Selection. *Adv. Immunol.* 88:235-65:235-265.
15. Levisetti, M. G., Lewis, D. M., Suri, A., and Unanue, E. R. 2008. Weak proinsulin peptide-major histocompatibility complexes are targeted in autoimmune diabetes in mice. *Diabetes.* 57:1852-1860.
16. Levisetti, M. G., Suri, A., Petzold, S. J., and Unanue, E. R. 2007. The insulin-specific T cells of nonobese diabetic mice recognize a weak MHC-binding segment in more than one form. *J Immunol.* 178:6051-6057.
17. Homann, D., and Eisenbarth, G. S. 2006. An immunologic homunculus for type 1 diabetes. *J. Clin. Invest.* 116: 1212-1215.

18. Boulard, O., Damotte, D., Deruytter, N., Fluteau, G., Carnaud, C., and Garchon, H. J. 2002. An interval tightly linked to but distinct from the h2 complex controls both overt diabetes (idd16) and chronic experimental autoimmune thyroiditis (ceat1) in nonobese diabetic mice. *diab* 51:2141-2147.
19. Aoki, C. A., Borchers, A. T., Ridgway, W. M., Keen, C. L., Ansari, A. A., and Gershwin, M. E. 2005. NOD mice and autoimmunity. *Autoimmun. Rev.* 4:373-379.
20. Kobayashi, M., Jasinski, J., Liu, E., Li, M., Miao, D., Zhang, L., Yu, L., Nakayama, M., and Eisenbarth, G. S. 2008. Conserved T cell receptor alpha-chain induces insulin autoantibodies. *Proc. Natl. Acad. Sci. U.S.A.* 105: 10090-10094.
21. Crawford, F., Huseby, E., White, J., Marrack, P., and Kappler, J. W. 2004. Mimotopes for Alloreactive and Conventional T Cells in a Peptide-MHC Display Library. *PLoS. Biol.* 2:E90.

What is claimed is:

1. An isolated antibody that specifically binds to a protein complex comprising I-A$^{g7}$ Class II MHC molecule and a peptide selected from the group consisting of
SEQ ID NO:2 (VEALYLVCGERG),
SEQ ID NO:3 (VEALYLVCGER),
SEQ ID NO:8 (VERLYLVAGEE),
SEQ ID NO:4 (LREALYLVAE),
SEQ ID NO:5 (VRALYLVAGE),
SEQ ID NO:6 (ERLYLVAGEE),
SEQ ID NO:7 (ARYLVAGERE), and
SEQ ID NO:9 (EALYLVCGER).

2. The isolated antibody of claim 1, wherein the antibody is humanized.

3. The isolated antibody of claim 1, wherein the antibody is Fab, Fab', F(ab')2, or scFv fragment.

4. The isolated antibody of claim 1, wherein the antibody is monoclonal.

* * * * *

```
                             SEQUENCE LISTING

<160> NUMBER OF SEQ ID NOS: 12

<210> SEQ ID NO 1
<211> LENGTH: 15
<212> TYPE: PRT
<213> ORGANISM: Homo sapiens

<400> SEQUENCE: 1

Ser His Leu Val Glu Ala Leu Tyr Leu Val Cys Gly Glu Arg Gly
1               5                   10                  15

<210> SEQ ID NO 2
<211> LENGTH: 12
<212> TYPE: PRT
<213> ORGANISM: Homo sapiens

<400> SEQUENCE: 2

Val Glu Ala Leu Tyr Leu Val Cys Gly Glu Arg Gly
1               5                   10

<210> SEQ ID NO 3
<211> LENGTH: 11
<212> TYPE: PRT
<213> ORGANISM: Homo sapiens

<400> SEQUENCE: 3

Val Glu Ala Leu Tyr Leu Val Cys Gly Glu Arg
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 4

Leu Arg Glu Ala Leu Tyr Leu Val Ala Glu
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 5

Val Arg Ala Leu Tyr Leu Val Ala Gly Glu
1               5                   10

<210> SEQ ID NO 6
<211> LENGTH: 10
<212> TYPE: PRT
<213> ORGANISM: Artificial Sequence
```

```
<220> FEATURE:
<223> OTHER INFORMATION: Synthetic Peptide

<400> SEQUENCE: 6

Glu Arg Leu Tyr Leu Val Ala Gly Glu Glu
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 7

Ala Arg Tyr Leu Val Ala Gly Glu Arg Glu
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 8

Val Glu Arg Leu Tyr Leu Val Ala Gly Glu Glu
1               5                   10

<210> SEQ ID NO 9
<211> LENGTH: 10
<212> TYPE: PRT
<213> ORGANISM: Homo sapiens

<400> SEQUENCE: 9

Glu Ala Leu Tyr Leu Val Cys Gly Glu Arg
1               5                   10

<210> SEQ ID NO 10
<211> LENGTH: 13
<212> TYPE: PRT
<213> ORGANISM: Gallus gallus

<400> SEQUENCE: 10

Met Lys Arg His Gly Leu Asp Asn Tyr Arg Gly Tyr Gly
1               5                   10

<210> SEQ ID NO 11
<211> LENGTH: 17
<212> TYPE: PRT
<213> ORGANISM: Artificial Sequence
<220> FEATURE:
<223> OTHER INFORMATION: Synthetic Linker Peptide

<400> SEQUENCE: 11

Gln Ala Gly Gly Gly Ser Leu Val Pro Arg Gly Ser Gly Gly Gly Gly
1               5                   10                  15

Ser

<210> SEQ ID NO 12
<211> LENGTH: 15
<212> TYPE: PRT
<213> ORGANISM: Artificial Sequence
<220> FEATURE:
<223> OTHER INFORMATION: Synthetic Linker Peptide
```

```
<400> SEQUENCE: 12

Gly Gly Gly Ser Leu Val Pro Arg Gly Ser Gly Gly Gly Ser
1               5               10              15
```